US009591978B2

(12) United States Patent
Friedhoff

(10) Patent No.: US 9,591,978 B2
(45) Date of Patent: Mar. 14, 2017

(54) METHODS AND COMPOSITIONS FOR PRE-SCREENING PATIENTS FOR TREATMENT WITH NORIBOGAINE

(71) Applicant: DemeRX, Inc., Fort Lauderdale, FL (US)

(72) Inventor: Lawrence Friedhoff, River Vale, NJ (US)

(73) Assignee: DEMERX, INC., Fort Lauderdale, FL (US)

( * ) Notice: Subject to any disclaimer, the term of this patent is extended or adjusted under 35 U.S.C. 154(b) by 0 days.

(21) Appl. No.: 14/624,307

(22) Filed: Feb. 17, 2015

(65) Prior Publication Data

US 2015/0257667 A1 Sep. 17, 2015

Related U.S. Application Data

(60) Provisional application No. 61/952,744, filed on Mar. 13, 2014, provisional application No. 62/005,858, filed on May 30, 2014.

(51) Int. Cl.
*A61B 5/04* (2006.01)
*A61K 31/55* (2006.01)
*A61B 5/0452* (2006.01)
*A61B 5/00* (2006.01)

(52) U.S. Cl.
CPC ........ *A61B 5/04012* (2013.01); *A61B 5/0452* (2013.01); *A61K 31/55* (2013.01); *A61B 5/4848* (2013.01)

(58) Field of Classification Search
CPC ...................................................... A61B 5/04
USPC ................................................... 514/214.02
See application file for complete search history.

(56) References Cited

U.S. PATENT DOCUMENTS

| | | | |
|---|---|---|---|
| 4,626,539 A | 12/1986 | Aungst et al. |
| 4,806,341 A | 2/1989 | Chien et al. |
| 5,149,538 A | 9/1992 | Granger et al. |
| 5,591,738 A | 1/1997 | Lotsof |
| 5,616,575 A | 4/1997 | Efange et al. |
| 6,348,456 B1 | 2/2002 | Mash et al. |
| 6,416,793 B1 | 7/2002 | Zeligs et al. |
| 6,933,308 B2 | 8/2005 | Boy et al. |
| 7,220,737 B1 | 5/2007 | Mash |
| 7,754,710 B2 | 7/2010 | Mash |
| 8,178,524 B2 | 5/2012 | Mash |
| 8,362,007 B1 | 1/2013 | Mash et al. |
| 8,637,648 B1 | 1/2014 | Mash et al. |
| 8,741,891 B1 | 6/2014 | Mash |
| 8,853,201 B2 | 10/2014 | Gless et al. |
| 9,045,481 B2 | 6/2015 | Mash et al. |
| 2003/0153552 A1 | 8/2003 | Mash et al. |
| 2003/0194438 A1 | 10/2003 | Prescott et al. |
| 2006/0229293 A1 | 10/2006 | Lotsof |
| 2007/0185085 A1 | 8/2007 | Mash |
| 2010/0311722 A1 | 12/2010 | Mash |
| 2010/0311723 A1 | 12/2010 | Mash |
| 2010/0311725 A1 | 12/2010 | Mash |
| 2012/0083485 A1 | 4/2012 | Mash |
| 2012/0253037 A1 | 10/2012 | Moriarty et al. |
| 2013/0011444 A1 | 1/2013 | Zebala |
| 2013/0072472 A1 | 3/2013 | Gless et al. |
| 2013/0131046 A1 | 5/2013 | Moriarty et al. |
| 2013/0165414 A1 | 6/2013 | Gless et al. |
| 2013/0165425 A1 | 6/2013 | Gless et al. |
| 2013/0165647 A1 | 6/2013 | Moriarty et al. |
| 2013/0211073 A1 | 8/2013 | Moriarty |
| 2013/0211074 A1 | 8/2013 | Moriarty |
| 2013/0296823 A1 | 11/2013 | Melker et al. |
| 2013/0303756 A1 | 11/2013 | Mash et al. |
| 2013/0311725 A1 | 11/2013 | Greenhalgh |
| 2014/0179685 A1 | 6/2014 | Mash et al. |
| 2014/0187655 A1 | 7/2014 | Mash et al. |
| 2014/0288056 A1 | 9/2014 | Friedhoff |
| 2014/0315891 A1 | 10/2014 | Mash |
| 2014/0357741 A1 | 12/2014 | Mash et al. |
| 2015/0045350 A1 | 2/2015 | Friedhoff |
| 2015/0231146 A1 | 8/2015 | Friedhoff |
| 2015/0238503 A1 | 8/2015 | Maillet et al. |
| 2015/0246055 A1 | 9/2015 | Friedhoff |
| 2015/0258105 A1 | 9/2015 | Maillet et al. |
| 2015/0258106 A1 | 9/2015 | Friedhoff |
| 2015/0258107 A1 | 9/2015 | Friedhoff |
| 2015/0258108 A1 | 9/2015 | Maillet et al. |
| 2015/0258111 A1 | 9/2015 | Maillet et al. |
| 2015/0258113 A1 | 9/2015 | Friedhoff |
| 2015/0258114 A1 | 9/2015 | Friedhoff |
| 2015/0342959 A1 | 12/2015 | Friedhoff |
| 2016/0008372 A1 | 1/2016 | Weis |
| 2016/0038508 A1 | 2/2016 | Perry et al. |
| 2016/0220579 A1 | 8/2016 | Weis et al. |

FOREIGN PATENT DOCUMENTS

| | | |
|---|---|---|
| WO | WO-96/03127 A1 | 2/1996 |
| WO | WO-99/11250 | 3/1999 |
| WO | WO-2012/012764 A1 | 1/2012 |

(Continued)

OTHER PUBLICATIONS

U.S. Appl. No. 13/593,454, filed Aug. 23, 2012, Moriarty et al.
Australian New Zealand Clinical Trials Registry ACTRN12612000821897, 2012.
Calsyn et al., "Slow tapering from methadone maintenance in a program encouraging indefinite maintenance," Journal of Substance Abuse Treatment, (2006), 30:159-163.
Donnelly, J.R., "The Need for Ibogaine in Drug and Alcohol Addiction Treatment," Journal of Legal Medicine, (2011), 32:93-114.
Eap et al., "Interindividual Variability of the Clinical Pharmacokinetics of Methadone," Clinical Pharmacokinetics, (2002), 41(14):1153-1193.

(Continued)

*Primary Examiner* — Taofiq A Solola
(74) *Attorney, Agent, or Firm* — Foley & Lardner LLP

(57) ABSTRACT

This invention is directed to a method for pre-screening an opioid-addicted patient to determine the patient's tolerance for a therapeutic dose of noribogaine.

10 Claims, 9 Drawing Sheets

(56) References Cited

FOREIGN PATENT DOCUMENTS

| WO | WO-2012/103028 | 8/2012 |
|---|---|---|
| WO | WO-2012/135047 | 10/2012 |
| WO | WO-2013/040471 | 3/2013 |
| WO | WO-2013/085849 | 6/2013 |
| WO | WO-2013/085922 A1 | 6/2013 |
| WO | WO-2013/112622 | 8/2013 |
| WO | WO-2013/112673 | 8/2013 |
| WO | WO-2014/019692 | 2/2014 |
| WO | WO-2014/144508 | 9/2014 |
| WO | WO-2015/126434 | 8/2015 |
| WO | WO-2015/126836 | 8/2015 |
| WO | WO-2015/195673 | 12/2015 |
| WO | WO-2016/086194 | 6/2016 |
| WO | WO-2016/134019 | 8/2016 |

OTHER PUBLICATIONS

Huffman, et al., "A Formal Synthesis of (±)-Ibogamine", J. Org. Chem., (1985), 50:1460-1464.
International Preliminary Report on Patentability dated Sep. 24, 2015 for PCT Application No. PCT/US2014/028946.
International Preliminary Report on Patentability for PCT/US2013/069235, mailed Sep. 24, 2015.
Jaffe. "Drug Addiction and Drug Abuse", Goodman and Gilman's The Pharmacological Basis of Therapeutics, 8th Ed., date unknown, pp. 520-523 & pp. 559-568.
Khan et al., "Long QT syndrome: Diagnosis and management", American Heart Journal, 2002, 143(1):7-14.
Krantz et al., "QTc Interval Screen in Methadone Treatment," Annals of Internal Medicine, 2009, American College of Physicians, vol. 150, pp. 387-395.
Kubiliene, et al., "Acute toxicity of ibogaine and noribogaine," Medicina (Kaunas), (2008), 44(12):984-988.
Maillet et al., "Noribogaine is a G-protein biased k-opioid receptor agonist", Neuropharmacology, 2015, 99, pp. 675-688.
Mitchell et al., "Temperature and the cold pressor test", J. Pain, 2004, 5:233-237.
PCT International Search Report and Written Opinion dated Mar. 10, 2014 in related PCT Patent Application No. PCT/US13/69235.
PCT International Search Report and Written Opinion for Appl No. PCT/US2015/016186 dated Apr. 24, 2015 5 Pages.
PCT International Search Report and Written Opinion for Appl. No. PCT/US2014/019692 dated Nov. 18, 2014.
Pearl et al., "Radioligand-binding Study of Noribogaine, A Likely Metabolite of Ibogaine", Brain Research, 1995, 675:342-344.
Stichering, Christian, Methadone-induced Torsade de pointes tachycardias, Swiss Med Wkly, 2005; vol. 135, pp. 282-285.
Weiss et al., "Neurobiology of craving, conditioned reward and relapse", Current Opinion in Pharmacology, 2005, 5:9-19.
Zubaran et a., "Noribogaine Generalization to the Ibogaine Stimulus: Correlation with Noribogaine Concentration in Rat Brain", Neuropsychopharmacology, 1999, vol. 21, pp. 119-126.
Bhargava, et al., "Effects of noribogaine on the development of tolerance to antinociceptive action of morphine in mice," Brain Research, (1997), 771:343-346.
Bhargava, et al., "Effects of ibogaine and noribogaine on the antinociceptive action of µ-, δ- and k-opioid receptor agonists in mice," Brain Research, (1997), 752:234-238.
Cao, et al., "Effects of ibogaine on the development of tolerance to antinociceptive action of µ-, δ- and k-opioid receptor agonists in mice," Brain Research, (1997), 752:250-254.
Breen, et al., "Cessation of Methadone Maintenance Treatment Using Buprenorphine: transfer from methadone to buprenorphine and subsequent buprenorphine reductions", Drug and Alcohol Dependence, 71 (2003), pp. 49-55.
Hoelen et al., Long-QT Syndrome Induced by the Antiaddiction Drug Ibogaine, Jan. 15, 2009, N. Engl J Med, 360(3), pp. 308-309.
International Search Report and Written Opinion Application No. PCT/US2015/062783 (364105-3860), mail date Feb. 9, 2016, 16 pages.
Kroupa, et al., "Ibogaine in the 21st Century: Boosters, Tune-ups and Maintenance," MAPS, (2005), 15(1):21-24.
New Zealand Ministry of Health, Prescriber Update (2010), 31(4), pp. 27-29.
PCT International Preliminary Report on Patentability for PCT Patent Application No. PCT/US14/19692, dated Feb. 1, 2016 (364105-2710), 19 pages.
Popik et. al. "100 Years of Ibogaine: Neourochemical and Pharmacological Actions of a Putative Anti-addictive Drug." Pharmacological Reviews (1995) 47:235-253.
Sharma et. al. "Enhancement of Morphine Antinociception by Ibogaine and Noribogaine in Morphine-tolerant Mice," Pharmacology (1998), 57:229232.
PCT International Search Report dated Aug. 12, 2016 in related PCT Patent Application No. PCT/US2016/031932.
Chang et al. "Noribogaine reduces nicotine self-administration in rats," Journal of Pyschopharmacology, May 20, 2015 (May 20, 2015), vol. 29, No. 6, pp. 704-711.
European Search Report dated Jul. 22, 2016 for related Application No. EP 14764408.2.
PCT International Preliminary Report on Patentability for related application No. PCT/US15/016186, dated Sep. 1, 2016.
PCT International Search Report and Written Opinion dated Jun. 10, 2016 in related PCT Patent Application No. PCT/US16/18273.

Box includes values representing 25% - 75% quartiles. Diamond = median; crossbar in box = mean; whiskers = values within standard deviation of mid-quartiles. No outliers present.

Mean Change in Total OOWS Score Over First 6 Hrs Following Dosing and Prior to OST Resumption Mean AUC(0-6) (Actual Time) of the OOWS Total Score Change from Baseline Using actual time of assessment out to 6 hrs

METHODS AND COMPOSITIONS FOR PRE-SCREENING PATIENTS FOR TREATMENT WITH NORIBOGAINE

CROSS-REFERENCE TO RELATED APPLICATIONS

This application claims priority to U.S. Provisional Application Nos. 61/952,744, filed Mar. 13, 2014, and 62/005,858, filed May 30, 2014, which are incorporated herein by reference in their entirety.

FIELD OF THE INVENTION

This invention is directed to a method for pre-screening an opioid-addicted patient to determine the patient's tolerance for a therapeutic dose of noribogaine.

STATE OF THE ART

Substance addiction is a serious public health problem throughout the world. Heroin and other opioids, including prescription painkillers, are widely abused and account for a large percentage of illicit drug use. Opioid use is also linked to approximately 50% of violent crimes in the United States and costs the U.S. economy billions of dollars per year.

Acute withdrawal from drug dependence is characterized by dramatic and traumatic symptoms, including sweating, racing heart, palpitations, muscle tension, tightness in the chest, difficulty breathing, tremor, nausea, vomiting, diarrhea, grand mal seizures, heart attacks, strokes, hallucinations and delirium tremens (DTs). Once acute withdrawal symptoms have subsided, post-acute withdrawal syndrome can last for months or years. Post-acute withdrawal symptoms include fatigue, depression, lack of motivation, and increased pain sensitivity.

SUMMARY

Noribogaine induces side effects in some patients. Methods are needed for pre-screening an opioid-addicted patient to determine the patient's tolerance for a therapeutic dose of noribogaine.

Noribogaine is administered to ameliorate acute and post-acute withdrawal symptoms. In particular, initial testing of noribogaine therapy with methadone addicted patients indicates that a single 120 mg dosing of noribogaine generally provides a meaningful therapeutic response, whereas a single 60 mg dosing of noribogaine generally does not provide a meaningful therapeutic response. It follows that a single 90 mg dose of noribogaine shows some therapy but is sub-therapeutic for commercial purposes.

The use of noribogaine may impart a dose dependent prolongation of the treated patient's QT interval, rendering higher dosing of noribogaine unacceptable. A prolonged QT interval is a marker of potential Torsades de Pointes, a serious arrhythmia that can result in death.

Unexpectedly, it was discovered that noribogaine behaves in a linear pattern regarding QT interval prolongation. For example, doubling the dose of noribogaine will result in about a doubling of the QT interval prolongation in the patient. As such, QT interval and QT interval prolongation data obtained from a sub-therapeutic dose of less than 120 mg of noribogaine, such as about 90 mg, can be used as a predictor of the patient's tolerance for therapeutic noribogaine treatment at the therapeutic dose of 120 mg. This is possible because the QT interval and QT interval prolongation data obtained from a sub-therapeutic dose of less than 120 mg of noribogaine can be accurately extrapolated for a dose of 120 mg noribogaine without subjecting the patient to a potentially life-threatening side effect at the therapeutic dosage.

As initially noted above, opioid-addicted patients treated with 120 mg noribogaine exhibit a significantly longer time to resumption of opioid substitution therapy than patients treated with 60 mg. Patients receiving 120 mg noribogaine also exhibit variable QT interval prolongation with an average prolongation of approximately 38 milliseconds (ms). Some patients exhibit QT interval prolongation of greater than 50 ms, or a QT interval of greater than 500 ms. A patient with a QT interval that is greater than 500 ms, or is prolonged more than 50 ms, is at high risk of ventricular tachyarrhythmia and possibly death.

Provided is a pre-screening method for predicting which patients are eligible for noribogaine therapy based on those who exhibit an unacceptable QT interval prolongation or a QT interval of over 500 milliseconds when treated with noribogaine. This method for predicting either an unacceptable QT interval prolongation of greater than 50 milliseconds or a QT interval of greater than 500 milliseconds can be used as a means of using sub-therapeutic doses (less than 120 mg) of noribogaine to screen out such patients before therapeutic doses (120 mg) of noribogaine therapy are initiated.

As will be apparent to the skilled artisan upon reading this disclosure, the present invention provides a method for pre-screening an opioid-addicted patient, or another patient in need of treatment or prevention as provided herein, to determine the patient's tolerance for a therapeutic dose of noribogaine.

In one aspect, provided is a method for screening an opioid-addicted patient to determine the patient's tolerance for a therapeutic dose of noribogaine or pharmaceutically acceptable salt and/or solvate thereof, the method comprising:

measuring the patient's pre-administration QT interval;
  administering to the patient a sub-therapeutic dose of noribogaine or pharmaceutically acceptable salt thereof;
  measuring the patient's post-administration QT interval;
  determining the difference between pre-administration QT interval and post-administration QT interval to determine a first prolongation;
  estimating a second prolongation based on the first prolongation, wherein the second prolongation is the estimated QT interval prolongation expected to be observed in the patient upon administration of a therapeutic dose of noribogaine;
  determining the patient's tolerance for the therapeutic dose of noribogaine; and
  administering to the patient the therapeutic dose of noribogaine or discontinuing noribogaine treatment, wherein a therapeutic dose is administered if the second prolongation is estimated to be less than about 50 ms.

In another embodiment, the therapeutic dose provides an average serum concentration of 50 ng/mL to 180 ng/mL, said concentration being sufficient to inhibit or ameliorate opioid addiction while resulting in prolongation of the patient's QT interval of less than about 50 ms.

In another embodiment, the method further comprises:
a) administering an initial dose of noribogaine, noribogaine derivative, or pharmaceutically acceptable salt or solvate thereof, wherein the initial dose provides an average serum concentration of 50 ng/mL to 180 ng/mL; and b) administering at least one additional dose of noribogaine, noribogaine derivative, or pharmaceutically acceptable salt or solvate thereof, such that the at least one additional dose maintains the average serum concentration of 50 ng/mL to 180 ng/mL for a period of time.

In another embodiment, the therapeutic dose is administered in one or more dosings. In another embodiment, the sub-therapeutic dose is administered in one or more dosings. In another embodiment, the sub-therapeutic dose is 80% or less than the therapeutic dose. In another embodiment, the sub-therapeutic dose is 70% or less than the therapeutic dose. In another embodiment, the sub-therapeutic dose is between 60 mg and 100 mg. In another embodiment, the sub-therapeutic dose is about 90 mg.

DETAILED DESCRIPTION

Figure 1:
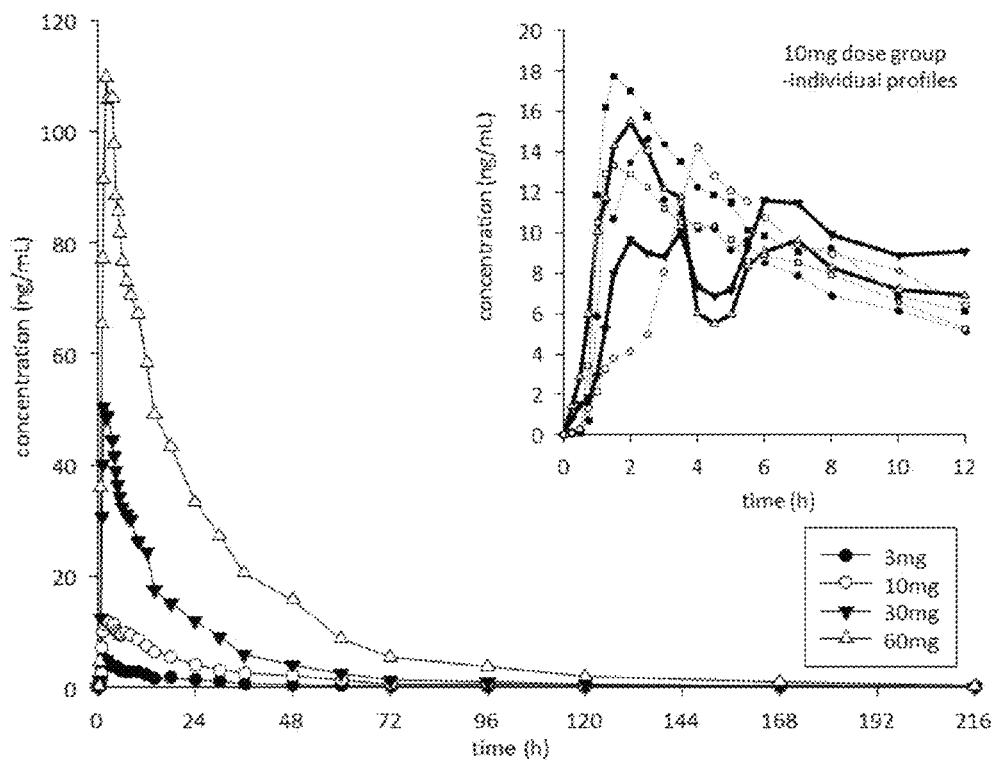
FIG. 1 represents mean noribogaine concentration-time profiles in healthy patients after single oral dosing with 3, 10, 30 or 60 mg doses. Inset: Individual concentration-time profiles from 0-12 h after a 10 mg dose.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

DEFINITIONS

It must be noted that as used herein and in the appended claims, the singular forms "a", "an", and "the" include plural referents unless the context clearly dictates otherwise. Thus, for example, reference to "a compound" includes a plurality of compounds.

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 20%, 10%, 5%, 1%, or any subrange or subvalue there between. Preferably, the term "about" when used with regard to a dose amount means that the dose may vary by +/−20%. For example, "about 2 mg/kg noribogaine" indicates that a patient may be administered a dose of noribogaine between 1.6 mg/kg and 2.4 mg/kg. In another example, about 120 mg per unit dose of noribogaine indicates that the unit dose may range from 96 mg to 144 mg.

"Administration" refers to introducing an agent, such as noribogaine, into a patient. Typically, an effective amount is administered, which amount can be determined by the treating physician or the like. Any route of administration, such as oral, topical, subcutaneous, peritoneal, intra-arterial, inhalation, vaginal, rectal, nasal, introduction into the cerebrospinal fluid, or instillation into body compartments can be used. The agent, such as noribogaine, may be administered by direct blood stream delivery, e.g. sublingual, buccal, intranasal, or intrapulmonary administration.

The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient.

"Periodic administration" or "periodically administering" refers to multiple treatments that occur on a daily, weekly, or monthly basis. Periodic administration may also refer to administration of an agent, such as noribogaine one, two, three, or more times per day. Administration may be via transdermal patch, gum, lozenge, sublingual tablet, intranasal, intrapulmonary, oral administration, or other administration.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

"Noribogaine" refers to the compound:

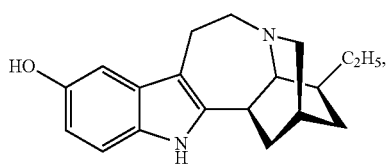

as well as noribogaine derivatives or pharmaceutically acceptable salts and pharmaceutically acceptable solvates thereof. It should be understood that where "noribogaine" is mentioned herein, one more polymorphs of noribogaine can be utilized and are contemplated. In some embodiments, noribogaine is noribogaine glucuronide. Noribogaine can be prepared by demethylation of naturally occurring ibogaine:

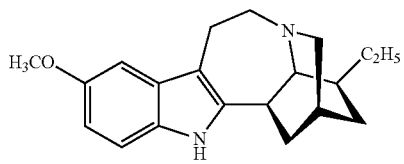

which is isolated from *Tabernanth iboga*, a shrub of West Africa. Demethylation may be accomplished by conventional techniques such as by reaction with boron tribromide/methylene chloride at room temperature followed by conventional purification. See, for example, Huffman, et al., J. Org. Chem. 50:1460 (1985), which incorporated herein by reference in its entirety. Noribogaine can be synthesized as described, for example in U.S. Patent Pub. Nos. 2013/0165647, 2013/0303756, and 2012/0253037, PCT Patent Publication No. WO 2013/040471 (includes description of making noribogaine polymorphs), and U.S. patent application Ser. No. 13/593,454, each of which is incorporated herein by reference in its entirety.

"Noribogaine derivatives" refer to, without limitation, esters or O-carbamates of noribogaine, or pharmaceutically acceptable salts and/or solvates of each thereof. Also encompassed within this invention are derivatives of noribogaine that act as prodrug forms of noribogaine. A prodrug is a pharmacological substance administered in an inactive (or significantly less active) form. Once administered, the prodrug is metabolized in vivo into an active metabolite. Noribogaine derivatives include, without limitation, those compounds set forth in U.S. Pat. Nos. 6,348,456 and 8,362,007; as well as in U.S. patent application Ser. No. 13/165,626; and US Patent Application Publication Nos. US2013/0131046; US2013/0165647; US2013/0165425; and US2013/0165414; all of which are incorporated herein by reference. Non-limiting examples of noribogaine derivatives encompassed by this invention are given in more detail in the "Compositions" section below.

In some embodiments, the methods of the present disclosure entail the administration of a prodrug of noribogaine that provides the desired maximum serum concentrations and efficacious average noribogaine serum levels. A prodrug of noribogaine refers to a compound that metabolizes, in vivo, to noribogaine. In some embodiments, the prodrug is selected to be readily cleavable either by a cleavable linking arm or by cleavage of the prodrug entity that binds to noribogaine such that noribogaine is generated in vivo. In one preferred embodiment, the prodrug moiety is selected to facilitate binding to the μ and/or κ receptors in the brain either by facilitating passage across the blood brain barrier or by targeting brain receptors other than the μ and/or κ receptors. Examples of prodrugs of noribogaine are provided in U.S. patent application Ser. No. 13/165,626, the entire content of which is incorporated herein by reference.

This invention is not limited to any particular chemical form of noribogaine or noribogaine derivative, and the drug may be given to patients either as a free base, solvate, or as a pharmaceutically acceptable acid addition salt. In the latter case, the hydrochloride salt is generally preferred, but other salts derived from organic or inorganic acids may also be used. Examples of such acids include, without limitation, those described below as "pharmaceutically acceptable salts" and the like.

"Pharmaceutically acceptable composition" refers to a composition that is suitable for administration to a mammal, preferably a human. Such compositions include various excipients, diluents, carriers, and such other inactive agents well known to the skilled artisan.

"Pharmaceutically acceptable salt" refers to pharmaceutically acceptable salts, including pharmaceutically acceptable partial salts, of a compound, which salts are derived from a variety of organic and inorganic counter ions well known in the art and include, by way of example only, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, oxalic acid and the like, and when the molecule contains an acidic functionality, include, by way of example only, sodium, potassium, calcium, magnesium, ammonium, tetraalkylammonium, and the like.

"Therapeutically effective amount" or "therapeutic amount" refers to an amount of a drug or an agent that, when administered to a patient suffering from a condition, will have the intended therapeutic effect, e.g., alleviation, amelioration, palliation or elimination of one or more manifestations of the condition in the patient. The therapeutically effective amount will vary depending upon the patient and the condition being treated, the weight and age of the subject, the severity of the condition, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of noribogaine, in the context of treating opioid or opioid-like drug dependency, refers to an amount of noribogaine that attenuates the dependency and/or symptoms of acute withdrawal for at least 2 hours beyond control (placebo), at least 5 hours beyond control, and preferably at least 10 hours beyond control. In some embodiments, the therapeutically effective amount of noribogaine is a 120 mg dose.

A "therapeutic level" of a drug is an amount of noribogaine, noribogaine derivative, or pharmaceutical salt or solvate thereof that is sufficient to treat opioid or opioid-like drug addiction or to treat, prevent, or attenuate acute withdrawal symptoms, but not high enough to pose any significant risk to the patient. Therapeutic levels of drugs can be determined by tests that measure the actual concentration of the compound in the blood of the patient. This concentration is referred to as the "serum concentration." Where the serum concentration of noribogaine is mentioned, it is to be understood that the term "noribogaine" encompasses any form of noribogaine, including derivatives thereof.

A "sub-therapeutic level" of noribogaine or pharmaceutical salt and/or solvate thereof that is less than the therapeutic level described above. For example, the sub-therapeutic level of noribogaine may be e.g., 80%, 70%, 60%, 50%, 40%, 30%, 20%, or 10% less than a therapeutically effective amount (e.g., 120 mg) of noribogaine, or any subvalue or subrange there between. Sub-therapeutic levels of noribogaine may coincide with "maintenance amounts" of noribogaine which are amounts, less than the therapeutically effective amount, that provide some attenuation and/or prevention of post-acute withdrawal syndrome in a patient. The maintenance amount of the compound is expected to be less than the therapeutically effective amount because the level of inhibition does not need to be as high in a patient who is no longer physically addicted to opioid or opioid-like drug.

As defined herein, a "prophylactically effective amount" of a drug is an amount, typically less than the therapeutically effective amount, that provides attenuation and/or prevention of a disease or disorder or symptoms of a disease or disorder in a patient. For example, the prophylactically effective amount of the compound is expected to be less than the therapeutically effective amount because the level of inhibition does not need to be as high in a patient who no longer has a disease or disorder or symptoms of a disease or disorder (e.g., no longer physically addicted to nicotine). For example, a prophylactically effective amount is preferably 90%, 80%, 70%, 60%, 50%, 40%, 30%, 20%, or 10% less than a therapeutically effective amount. However, a prophylactically effective amount may be the same as the therapeutically effective amount, for example when a patient who is physically addicted to nicotine is administered noribogaine to attenuate cravings for a period of time when nicotine use is not feasible. The prophylactically effective amount may vary for different a diseases or disorders or symptoms of different diseases or disorders.

As defined herein, a "maintenance amount" of a drug or an agent is an amount, typically less than the therapeutically effective amount that provides attenuation and/or prevention of syndrome disease or disorder or symptoms of a disease or disorder in a patient. The maintenance amount of the compound is expected to be less than the therapeutically effective amount because the level of inhibition does not need to be as high in a patient who is no longer physically manifests a disease or disorder or symptoms of a disease or disorder. For example, a maintenance amount is preferably 90%, 80%, 70%, 60%, 50%, 40%, 30%, 20%, or 10% less than a therapeutically effective amount, or any subvalue or subrange there between.

"Treatment," "treating," and "treat" are defined as acting upon a disease, disorder, or condition with an agent, such as noribogaine, to reduce or ameliorate harmful or any other undesired effects of the disease, disorder, or condition and/or its symptoms. "Treatment," as used herein, covers the treatment of a human patient, and includes: (a) reducing the risk of occurrence of the condition in a patient determined to be predisposed to the condition but not yet diagnosed as having the condition, (b) impeding the development of the condition, and/or (c) relieving the condition, i.e., causing regression of the condition and/or relieving one or more symptoms of the condition. "Treating" or "treatment of" a condition or patient refers to taking steps to obtain beneficial or desired results, including clinical results such as the reduction of symptoms. For purposes of this invention, beneficial or desired clinical results include, but are not limited to: treating opioid or opioid-like drug addiction; treating, preventing, and/or attenuating acute withdrawal symptoms; treating, preventing, and/or attenuating long-term (post-acute) withdrawal symptoms; and preventing relapse of opioid or opioid-like drug use.

As used herein, the term "patient" refers to mammals and includes humans and non-human mammals.

As used herein, the term "opiate" refers to naturally-occurring alkaloids found in the opium poppy. These include codeine, morphine, oripavine, pseudomorphine, and thebaine. Also included are opium, opium poppy, poppy straw, and extracts and concentrates thereof.

As used herein, the term "opioid" refers to naturally-occurring opiates and synthetic or semi-synthetic opioids that have psychoactive effects. Non-limiting examples include acetyl-alpha-methylphentanyl, acetylmethadol, alfentanil, allylprodine, alphacetylmethadol, alphamethadol, alpha-methylfentanyl, alpha-methylthiofentanyl, alphaprodine, anileridine, benzylmorphine, benzethidine, beta-cetylmethadol, beta-hydroxyfentanyl, beta-hydroxy-3-methylfentanyl, betameprodine, betacetylmethadol, beta-hydroxyfentanyl, beta-hydroxy-3-methylfentanyl, betameprodine, betamethadol, betaprodine, bezitramide, buprenorphine, butorphanol, carfentanil, clonitazene, codeine, desomorphine, dextromoramide, dextropropoxyphene, dezocine, diampromide, diamorphone, diethylthiambutene, dihydrocodeine, dihydroetorphine, dihydromorphine, dimenoxadol, dimepheptanol, dimethyl-thiambutene, dioxaphetyl butyrate, diphenoxylate, difenoxin, dipipanone, eptazocine, ethoheptazine, ethylmethylthiambutene, ethylmorphine, etonitazene, etorphine, etoxeridine, fentanyl, furethidine, heroin, hydrocodone, hydromorphone, hydroxypethidine, isomethadone, ketobemidone, levo-alphacetylmethadol, levomethorphan, levorphanol, levophenacylmorphan, levomoramide, lofentanil, loperamide, laudanum, meperidine, meptazinol, metazocine, methadone, 3-methylfentanyl, 3-methylthiofentanyl, metopon, morphine, morpheridine, MPPP (1-methyl-4-phenyl-4-propionoxypiperidine), myrophine, narceine, nicomorphine, noracymethadol, norlevorphanol, normethadone, nalorphine, nalbuphene, normorphine, norpipanone, opium, oxycodone, oxymorphone, papaveretum, para-fluorofentanyl, paregoric, PEPAP (1-(–2-phenethyl)-4-phenyl-4-acetoxypiperidine), pentazocine, phenadoxone, phenampromide, phenomorphan, phenazocine, phenoperidine, piminodine, piritramide, propheptazine, promedol, properidine, propiram, propoxyphene, racemoramide, racemethorphan, racemorphan, remifentanil, sufentanil, tapentadol, thiofentanyl, tilidine, tramadol, trimeperidine, mixtures of any of the foregoing, salts of any of the foregoing, derivatives of any of the foregoing, and the like. The term opioids also encompasses opioid intermediates, including 4-cyano-2-dimethylamino-4,4-diphenyl butane, 2-methyl-3-morpholino-1,1-diphenyl-propane-carboxylic acid, 4-cyano-1-methyl-4-phenylpiperidine, ethyl-4-phenylpiperidine-4-carboxylate, and 1-methyl-4-phenylpiperidine-4-carboxylic acid. Many opioids are Schedule I or Schedule II drugs in the US.

As used herein, the term "opioid-like drug" refers to any illicit drug that binds to one or more opioid receptor and causes opioid-like addiction. Acute and long-term withdrawal symptoms from cessation of use of such drugs may be similar to those from cessation of opioids. Opioid-like drugs include amphetamine, methamphetamine, ketamine, and cocaine.

As used herein, the term "QT interval" refers to the measure of the time between the start of the Q wave and the end of the T wave in the electrical cycle of the heart. Prolongation of the QT interval refers to an increase in the QT interval.

As used herein, the terms "addiction" and "dependence" are used interchangeably to refer to the patient's inability to stop using the opioid or opioid-like drug, even when it would be in his/her best interest to stop. The DSMIV-TR criteria for dependency include: Dependence or significant impairment or distress, as manifested by 3 or more of the following during a 12 month period:
1. Tolerance or markedly increased amounts of the substance to achieve intoxication or desired effect or markedly diminished effect with continued use of the same amount of substance
2. Withdrawal symptoms or the use of certain substances to avoid withdrawal symptoms
3. Use of a substance in larger amounts or over a longer period than was intended
4. Persistent desire or unsuccessful efforts to cut down or control substance use
5. Involvement in chronic behavior to obtain the substance, use the substance, or recover from its effects
6. Reduction or abandonment of social, occupational or recreational activities because of substance use
7. Use of substances even though there is a persistent or recurrent physical or psychological problem that is likely to have been caused or exacerbated by the substance.

A "pharmaceutically acceptable solvate" or "hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

As used herein the term "solvate" is taken to mean that a solid-form of a compound that crystallizes with one or more molecules of solvent trapped inside. A few examples of solvents that can be used to create solvates, such as pharmaceutically acceptable solvates, include, but are certainly not limited to, water, methanol, ethanol, isopropanol, butanol, C1-C6 alcohols in general (and optionally substituted), tetrahydrofuran, acetone, ethylene glycol, propylene glycol, acetic acid, formic acid, water, and solvent mixtures thereof. Other such biocompatible solvents which may aid in making a pharmaceutically acceptable solvate are well known in the art and applicable to the present invention. Additionally, various organic and inorganic acids and bases can be added or even used alone as the solvent to create a desired solvate. Such acids and bases are known in the art. When the solvent is water, the solvate can be referred to as a hydrate. Further, by being left in the atmosphere or recrystallized, the compounds of the present invention may absorb moisture, may include one or more molecules of water in the formed crystal, and thus become a hydrate. Even when such hydrates are formed, they are included in the term "solvate". Solvate also is meant to include such compositions where another compound or complex co-crystallizes with the compound of interest. The term "solvate" as used herein refers to complexes with solvents in which noribogaine is reacted or from which noribogaine is precipitated or crystallized. For example, a complex with water is known as a "hydrate". Solvates of noribogaine are within the scope of the invention. It will be appreciated by those skilled in organic chemistry that many organic compounds can exist in more than one crystalline form. For example, crystalline form may vary based on the solvate used. Thus, all crystalline forms of noribogaine or the pharmaceutically acceptable solvates thereof are within the scope of the present invention.

The therapeutically effective amount of the compound may be higher or lower, depending on the route of administration used. For example, when direct blood administration (e.g., sublingual, pulmonary and intranasal delivery) is used, a lower dose of the compound may be administered. In one aspect, a therapeutically effective amount of noribogaine or derivative is from about 50 ng to less than 100 μg per kg of body weight. Where other routes of administration are used, a higher dose of the compound may be administered. In one embodiment, the therapeutically effective amount of the compound is from greater than about 1 mg to about 8 mg per kg of body weight per day.

Methods for Patient Pre-Screening

As will be apparent to the skilled artisan upon reading this disclosure, the present invention provides a method for pre-screening an opioid-addicted patient to determine the patient's tolerance for a therapeutic dose of noribogaine.

Pre-screening of patients before treatment with noribogaine and/or monitoring of patients during noribogaine, noribogaine derivative, or pharmaceutically acceptable sald and/or solvate thereof treatment may be required to ensure that QT interval is not prolonged beyond a certain value. For example, QT interval greater than about 500 ms can be considered dangerous for individual patients. Pre-screening and/or monitoring may be necessary at high levels of noribogaine treatment.

In one aspect, provided is a method for screening an opioid-addicted patient to determine the patient's tolerance for a therapeutic dose of noribogaine or pharmaceutically acceptable salt and/or solvate thereof, the method comprising:

measuring the patient's pre-administration QT interval;
administering to the patient a sub-therapeutic dose of noribogaine or pharmaceutically acceptable salt thereof; and
measuring the patient's post-administration QT interval.

In some embodiments, the method further comprises one or more of:
determining the difference between pre-administration QT interval and post-administration QT interval to determine a first prolongation;
estimating a second prolongation based on the first prolongation, wherein the second prolongation is the estimated QT interval prolongation expected to be observed in the patient upon administration of a therapeutic dose of noribogaine;
determining the patient's tolerance for the therapeutic dose of noribogaine; and
administering to the patient the therapeutic dose of noribogaine or discontinuing noribogaine treatment, wherein a therapeutic dose is administered if the second prolongation is estimated to be less than about 50 ms.

In one embodiment, provided is a method for screening an opioid-addicted patient to determine the patient's tolerance for a therapeutic dose of noribogaine or pharmaceutically acceptable salt and/or solvate thereof, the method comprising:
measuring the patient's pre-administration QT interval;
administering to the patient a sub-therapeutic dose of noribogaine or pharmaceutically acceptable salt thereof;
measuring the patient's post-administration QT interval;
determining the difference between pre-administration QT interval and post-administration QT interval to determine a first prolongation;
estimating a second prolongation based on the first prolongation, wherein the second prolongation is the estimated QT interval prolongation expected to be observed in the patient upon administration of a therapeutic dose of noribogaine;
determining the patient's tolerance for the therapeutic dose of noribogaine; and
administering to the patient the therapeutic dose of noribogaine or discontinuing noribogaine treatment, wherein a therapeutic dose is administered if the second prolongation is estimated to be less than about 50 ms.

In one embodiment, a therapeutic dose is administered if the second prolongation is estimated to be less than about 40 ms. In one embodiment, a therapeutic dose is administered if the second prolongation is estimated to be less than about 30 ms. In one embodiment, a therapeutic dose is administered if the second prolongation is estimated to be less than about 20 ms. In one embodiment, a therapeutic dose is administered if the second prolongation is estimated to be less than about 10 ms.

In a preferred embodiment, a patient being screened to determine the patient's tolerance for a therapeutic dose of noribogaine or pharmaceutically acceptable salt and/or solvate thereof is monitored in a clinical setting. In one embodiment, a patient receiving a therapeutic dose of noribogaine is monitored in a clinical setting. Monitoring may be necessary to ensure the QT interval is not prolonged to an unacceptable degree. A "clinical setting" refers to an inpatient setting (e.g., inpatient clinic, hospital, rehabilitation facility) or an outpatient setting with frequent, regular monitoring (e.g., outpatient clinic that is visited daily to receive dose and monitoring). Monitoring includes monitoring of QT interval. Methods for monitoring of QT interval are well-known in the art, for example by ECG.

In one embodiment, a patient receiving a maintenance or therapeutic dose of noribogaine is not monitored in a clinical setting. In one embodiment, a patient receiving a maintenance or therapeutic dose of noribogaine is monitored periodically, for example daily, weekly, monthly, or occasionally.

In one embodiment, the therapeutic dose provides an average serum concentration of 50 ng/mL to 180 ng/mL, said concentration being sufficient to inhibit or ameliorate opioid addiction while resulting in prolongation of the patient's QT interval of less than a threshold, for example about 50 ms.

In a preferred embodiment, the therapeutic dose is about 120 mg noribogaine. In another embodiment, the therapeutic dose is between 70-120 mg noribogaine. In another embodiment, the therapeutic dose is between 100-150 mg noribogaine. In another embodiment, the therapeutic dose is more than 150 mg noribogaine. In one embodiment, the therapeutic dose is between 1 mg per kg body weight and 4 mg per kg body weight.

In one embodiment, the therapeutic dose is administered in one or more dosings, such as one, two, three, four, five or more dosings over one or more days.

In one embodiment, the sub-therapeutic dose is administered in one or more dosings, such as one, two, three, four, five or more dosings over one or more days.

In one embodiment, the sub-therapeutic dose of noribogaine may be e.g., 80%, 70%, 60%, 50%, 40%, 30%, 20%, or 10% less than a therapeutically effective dose (e.g., 120 mg) of noribogaine, or any subvalue or subrange there between.

In one embodiment, the sub-therapeutic dose of noribogaine may be e.g., 110 mg, 100 mg, 90 mg, 80 mg, 70 mg, 60 mg, 50 mg, 40 mg, 30 mg, 20 mg, 10 mg, 5 mg, 2 mg, 1 mg of noribogaine, or any subvalue or subrange there between.

In one embodiment, where the second prolongation is estimated to be greater than a threshold QT interval prolongation, the patient is administered a sub-therapeutic dose of noribogaine.

In one embodiment, where the second prolongation is estimated to be greater than a threshold QT interval prolongation, the patient is administered a therapeutic dose of noribogaine in multiple administrations. For example, where the therapeutic dose is 120 mg per day, 60 mg may be given every 12 hours. Without being limited by theory, it is believed that multiple administrations will lower the maximum serum concentration of noribogaine experienced by the patient, thereby reducing QT interval prolongation.

In one embodiment, where the second prolongation is estimated to be greater than a threshold QT interval prolongation, the patient is administered an initial dose of noribogaine, followed by one or more additional doses. In one embodiment, the initial dose is from 75 mg to 120 mg. In one embodiment, the one or more additional doses are lower than the initial dose. In one embodiment, the one or more additional doses are from 5 mg to 50 mg. In one embodiment, such a dosing regimen provides an average serum concentration of noribogaine of 50 ng/mL to 180 ng/mL. In one embodiment, such a dosing regimen provides an average serum concentration of noribogaine of 80 ng/mL to 100 ng/mL. In one embodiment, the one or more additional doses maintain an average serum concentration of 50 ng/mL to 180 ng/mL over a period of time. In one embodiment, the one or more additional doses maintain an average serum concentration of 80 ng/mL to 100 ng/mL over a period of time. In one embodiment, the one or more additional doses are administered periodically, such as every 4 hours, every 6 hours, every 8 hours, every 12 hours, or every 24 hours.

In one embodiment, the threshold QT interval prolongation is 50 ms. In one embodiment, the threshold QT interval prolongation is 40 ms. In one embodiment, the threshold QT interval prolongation is 30 ms. In one embodiment, the threshold QT interval prolongation is 20 ms. In one embodiment, the threshold QT interval prolongation is 10 ms.

In one embodiment, the therapeutic amount of noribogaine is sufficient to provide an average serum concentration of noribogaine from 50 ng/mL to 180 ng/mL, or 60 ng/mL to 180 ng/mL. In one embodiment, the therapeutic amount of noribogaine is sufficient to provide an average serum concentration of noribogaine from 50 ng/mL to 150 ng/mL, or 60 ng/mL to 150 ng/mL. In one embodiment, the therapeutic amount of noribogaine is sufficient to provide an average serum concentration of noribogaine from 50 ng/mL to 100 ng/mL, or 60 ng/mL to 100 ng/mL. In one embodiment, the therapeutic amount of noribogaine is sufficient to provide an average serum concentration of noribogaine from 80 ng/mL to 100 ng/mL The ranges include both extremes as well as any subranges between.

In one embodiment, prescreening of the patient comprises ascertaining that noribogaine treatment will not result in a maximum QT interval over about 500 ms. In one embodiment, prescreening of the patient comprises ascertaining that noribogaine treatment will not result in a maximum QT interval over about 470 ms. In one embodiment, prescreening comprises ascertaining that noribogaine treatment will not result in a maximum QT interval over about 450 ms. In one embodiment, prescreening comprises ascertaining that noribogaine treatment will not result in a maximum QT interval over about 420 ms. In one embodiment, prescreening comprises determining the patient's pre-treatment QT interval.

As it relates to pre-screening or pre-selection of patients, patients may be selected based on any criteria as determined by the skilled clinician. Such criteria may include, by way of non-limiting example, pre-treatment QT interval, pre-existing cardiac conditions, risk of cardiac conditions, age, sex, general health, and the like. The following are examples of selection criteria for disallowing noribogaine treatment or restricting dose of noribogaine administered to the patient: high QT interval before treatment (e.g., such that there is a risk of the patient's QT interval exceeding about 500 ms during treatment); congenital long QT syndrome; bradycardia; hypokalemia or hypomagnesemia; recent acute myocardial infarction; uncompensated heart failure; and taking other drugs that increase QT interval. In some embodiments, the methods can include selecting and/or administering/providing noribogaine to a patient that lacks one more of such criteria.

In one embodiment, this invention relates to pre-screening a patient to determine if the patient is at risk for prolongation of the QT interval beyond a safe level. In one embodiment, a patient at risk for prolongation of the QT interval beyond a safe level is not administered noribogaine. In one embodiment, a patient at risk for prolongation of the QT interval beyond a safe level is administered noribogaine at a limited dosage.

In one embodiment, this invention relates to monitoring a patient who is administered a therapeutic dose of noribogaine. In one embodiment, the dose of noribogaine is reduced if the patient has serious adverse side effects. In one embodiment, the noribogaine treatment is discontinued if the patient has serious adverse side effects. In one embodiment, the adverse side effect is a QT interval that is prolonged beyond a safe level. The determination of a safe level of prolongation is within the skill of a qualified clinician.

In one aspect, this invention relates to a method for treating an anxiety disorder, an impulse control disorder, or an anger/violence-related disorder, and/or treating or attenuating the symptoms thereof in a patient, comprising selecting a patient exhibiting symptoms of an anxiety disorder, impulse control disorder, or anger/violence-related disorder who is prescreened to evaluate the patient's expected tolerance for prolongation of QT interval, administering to the patient a dosage of noribogaine, noribogaine derivative, or pharmaceutically acceptable salt and/or solvate thereof that provides an average serum concentration of about 50 ng/mL to about 850 ng/mL, said concentration being sufficient to inhibit or ameliorate said disorder or symptoms while maintaining a QT interval of less than about 500 ms during said treatment. In some embodiments, the concentration is sufficient to attenuate said symptoms while maintaining a QT interval of less than about 470 ms during treatment. Preferably, the concentration is sufficient to attenuate said symptoms while maintaining a QT interval of less than about 450 ms during treatment. In one embodiment, the concentration is sufficient to attenuate said symptoms while maintaining a QT interval of less than about 420 ms during treatment.

In one aspect, this invention relates to a method for regulating food intake, and/or treating or attenuating food cravings, in a patient, comprising selecting an overweight or obese patient who is prescreened to evaluate the patient's expected tolerance for prolongation of QT interval, administering to the patient a dosage of noribogaine, noribogaine derivative, or pharmaceutically acceptable salt and/or solvate thereof that provides an average serum concentration of about 50 ng/mL to about 180 ng/mL, said concentration being sufficient to inhibit or ameliorate said disorder or symptoms while maintaining a QT interval of less than about 500 ms during said treatment.

Kit of Parts

One aspect of this invention is directed to a kit of parts for pre-screening an opioid-addicted patient to determine the patient's tolerance for a therapeutic dose of noribogaine, wherein the kit comprises a sub-therapeutic dosage of noribogaine or salt and/or solvate thereof and a means for administering the composition to a patient in need thereof. The means for administration to a patient can include, for example, any one or combination of a pharmaceutically acceptable formulation comprising noribogaine, or a noribogaine derivative, or a pharmaceutically acceptable salt or solvate thereof (e.g., a pill, transdermal patch, injectable, and the like, without limitation) and optionally a means for dispensing and/or administering the formulation (e.g., a syringe, a needle, an IV bag comprising the composition, a vial comprising the composition, an inhaler comprising the composition, etc, without limitation). In one embodiment, the kit of parts further comprises instructions for dosing and/or administration of the composition.

In some aspects, the invention is directed to a kit of parts for administration of a sub-therapeutic dose of noribogaine for pre-screening an opioid-addicted patient to determine the patient's tolerance for a therapeutic dose of noribogaine, the kit comprising multiple delivery vehicles, wherein each delivery vehicle contains a discrete amount of noribogaine and further wherein each delivery vehicle is identified by the amount of noribogaine provided therein; and optionally further comprising a dosing treatment schedule in a readable medium. In some embodiments, the dosing treatment schedule includes a sub-therapeutic amount of noribogaine (e.g., less than 120 mg). In some embodiments, the kit of parts includes a dosing treatment schedule that provides an attending clinician the ability to select a sub-therapeutic dosing regimen of noribogaine, according to the methods described herein, based on the sex of the patient, mass of the patient, and the serum level that the clinician desires to achieve. In some embodiments, the dosing treatment schedule further provides information corresponding to the volume of blood in a patient based upon weight (or mass) and sex of the patient. In an embodiment, the storage medium can include an accompanying pamphlet or similar written information that accompanies the unit dose form in the kit. In an embodiment, the storage medium can include electronic, optical, or other data storage, such as a non-volatile memory, for example, to store a digitally-encoded machine-readable representation of such information.

The term "delivery vehicle" as used herein refers to any formulation that can be used for administration of noribogaine to a patient. Non-limiting, exemplary delivery vehicles include caplets, pills, capsules, tablets, powder, liquid, or any other form by which the drug can be administered. Delivery vehicles may be intended for administration by oral, inhaled, injected, or any other means.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

In some aspects, the machine-readable medium comprises software that contains information regarding dosing schedules for the unit dose form of noribogaine and optionally other drug information. In some embodiments, the software may be interactive, such that the attending clinician or other medical professional can enter patient information. In a non-limiting example, the medical professional may enter the weight and sex of the patient to be treated, and the software program provides a recommended dosing regimen based on the information entered. The amount and timing of noribogaine recommended to be delivered will be within the dosages that result in the serum concentrations as provided herein.

In some embodiments, the kit of parts comprises multiple delivery vehicles in a variety of dosing options. For example, the kit of parts may comprise pills or tablets in multiple dosages, such as 120 mg, 90 mg, 60 mg, 30 mg, 20 mg, 10 mg, and/or 5 mg of noribogaine per pill. Each pill is labeled such that the medical professional and/or patient can easily distinguish different dosages. Labeling may be based on printing or embossing on the pill, shape of the pill, color of pill, the location of the pill in a separate, labeled compartment within the kit, and/or any other distinguishing features of the pill. In some embodiments, all of the delivery vehicles within a kit are intended for one patient. In some embodiments, the delivery vehicles within a kit are intended for multiple patients.

Sub-therapeutic and therapeutic doses of noibogaine may be achieved by transdermal, oral, or parenteral administration of noribogaine, noribogaine derivative, or a pharmaceutically acceptable salt and/or solvate thereof in unit dose form. Such unit dose form may conveniently be provided in transdermal patch, tablet, caplet, liquid or capsule form. In certain embodiments, the noribogaine is provided as noribogaine HCl, with dosages reported as the amount of free base noribogaine. In some embodiments, the noribogaine HCl is provided in hard gelatin capsules containing only noribogaine HCl with no excipients. In some embodiments, noribogaine is provided in saline for intravenous administration.

One aspect of this invention is directed to a kit of parts for the treatment, prevention, or attenuation of a disease or disorder or symptoms of a disease or disorder described herein, wherein the kit comprises a unit dose form of noribogaine, noribogaine derivative, or salt or solvate thereof. The unit dose form provides a patient with an average serum level of noribogaine of from about 50 ng/mL to about 180 ng/mL or about 60 ng/mL to about 180 ng/mL. The unit dose form provides a patient with an average serum level of noribogaine of from about 50 ng/mL to about 800 ng/mL or about 60 ng/mL to about 800 ng/mL. In one embodiment, the unit dose form provides a patient with an average serum level of noribogaine of from about 50 ng/mL to about 400 ng/mL or about 60 ng/mL to about 400 ng/mL. In one embodiment, the unit dose form provides a patient with an average serum level of noribogaine of from 80 ng/mL to 100 ng/mL.

In some embodiments, the unit dose of noribogaine, noribogaine derivative, or pharmaceutically acceptable salt or solvate thereof is from 20 mg to 120 mg. In one embodiment, the unit dose is 20 mg. In one embodiment, the unit dose is 30 mg. In one embodiment, the unit dose is 40 mg. In one embodiment, the unit dose is 50 mg. In one embodiment, the unit dose is 60 mg. In one embodiment, the unit dose is 70 mg. In one embodiment, the unit dose is 80 mg. In one embodiment, the unit dose is 90 mg. In one embodiment, the unit dose is 100 mg. In one embodiment, the unit dose is 110 mg. In one embodiment, the unit dose is 120 mg.

In some embodiments, the unit dose form comprises one or multiple dosages to be administered periodically, such as once, twice, three times, four times or five times daily with noribogaine or its prodrug. In some embodiments, the administration is once daily, or once every second day, once every third day, three times a week, twice a week, or once a week. The dosage and frequency of the administration depends on criteria including the route of administration, content of composition, age and body weight of the patient, condition of the patient, sex of the patient, without limitation, as well as by the severity of the addiction. Determination of the unit dose form providing a dosage and frequency suitable for a given patient can readily be made by a qualified clinician.

In some embodiments, the initial unit dose and one or more additional doses of noribogaine, noribogaine derivative, or salt or solvate thereof are provided as one or multiple dosages to be administered periodically, such as once, twice, three times, four times or five times daily with noribogaine or its prodrug. In some embodiments, the administration is once daily, or once every second day, once every third day, three times a week, twice a week, or once a week. The dosage and frequency of the administration depends on criteria including the route of administration, content of composition, age and body weight of the patient, condition of the patient, sex of the patient, without limitation, as well as by the severity of the addiction. Determination of the unit dose form providing a dosage and frequency suitable for a given patient can readily be made by a qualified clinician.

In one aspect, provided herein is a kit of parts comprising two or more doses of noribogaine, noribogaine derivative, or pharmaceutically acceptable salt or solvate thereof, wherein the two or more doses comprise an amount of noribogaine, noribogaine derivative, or pharmaceutically acceptable salt or solvate thereof that is sufficient to maintain a serum concentration of 50 ng/mL to 180 ng/mL when administered to a patient.

In one embodiment, one dose comprises an initial dose of noribogaine, noribogaine derivative, or pharmaceutically acceptable salt or solvate thereof, said initial dose being sufficient to achieve a therapeutic serum concentration when administered to a patient; and at least one additional dose, said additional dose sufficient to maintain a therapeutic serum concentration when administered to a patient, wherein the therapeutic serum concentration is between 50 ng/mL and 180 ng/mL In another embodiment, the initial dose is from 75 mg to 120 mg. In another embodiment, the at least one additional dose is from 5 mg to 25 mg.

Formulations

The disclosed methods relate to pharmaceutically acceptable formulations comprising a sub-therapeutic unit dose of noribogaine, noribogaine derivative, or pharmaceutically acceptable salt or solvate thereof, wherein the amount of noribogaine is sufficient to provide an average serum concentration of about 50 ng/mL to about 180 ng/mL when administered to a patient. In a preferred embodiment, the amount of noribogaine in a therapeutic dose is sufficient to provide an average serum concentration of about 80 ng/mL to about 100 ng/mL when administered to a patient. In some embodiments, each of the non-therapeutic or therapeutic unit dose of noribogaine is administered in one or more dosings. In one embodiment, the amount of noribogaine, noribogaine derivative, or pharmaceutically acceptable salt thereof is an amount that delivers an aggregate amount of noribogaine of about 50 ng to about 10 µg per kg body weight per day.

In some embodiments, non-therapeutic or therapeutic noribogaine formulations are designed for periodic administration, such as once, twice, three times, four times or five times daily with noribogaine or a pharmaceutically acceptable salt and/or solvate thereof. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made a qualified clinician.

In some embodiments, the unit dose of noribogaine is administered in one or more dosings.

This invention further relates to pharmaceutically acceptable formulations comprising a unit dose of noribogaine, noribogaine derivative, or pharmaceutically acceptable salt or solvate thereof, wherein the amount of noribogaine is sufficient to provide and/or maintain an average serum concentration of about 50 ng/mL to about 180 ng/mL when administered to a patient. In a preferred embodiment, the amount of noribogaine is sufficient to provide and/or maintain an average serum concentration of 80 ng/mL to 100 ng/mL when administered to a patient.

In some embodiments, the unit dose of noribogaine is administered in one or more dosings.

In one embodiment, the amount of noribogaine is sufficient to provide an average serum concentration of noribogaine from 50 ng/mL to 180 ng/mL, or 60 ng/mL to 180 ng/mL. In one embodiment, the amount of noribogaine is sufficient to provide an average serum concentration of noribogaine from 50 ng/mL to 150 ng/mL, or 60 ng/mL to 150 ng/mL. In one embodiment, the amount of noribogaine is sufficient to provide an average serum concentration of noribogaine from about 50 ng/mL to about 120 ng/mL, or about 60 ng/mL to about 120 ng/mL. In one embodiment, the amount of noribogaine is sufficient to provide an average serum concentration of noribogaine from about 50 ng/mL to about 100 ng/mL, or about 60 ng/mL to about 100 ng/mL. In one embodiment, the amount of noribogaine is sufficient to provide an average serum concentration of noribogaine from about 50 ng/mL to about 120 ng/mL, or about 60 ng/mL to about 120 ng/mL. In one embodiment, the amount of noribogaine is sufficient to provide an average serum concentration of noribogaine from about 50 ng/mL to about 100 ng/mL, or about 60 ng/mL to about 100 ng/mL. In one embodiment, the amount of noribogaine is sufficient to provide an average serum concentration of noribogaine from about 80 ng/mL to about 100 ng/mL. The ranges include both extremes as well as any subranges between.

In some embodiments, the initial unit dose of noribogaine, noribogaine derivative, or pharmaceutically acceptable salt or solvate thereof is from about 50 mg to about 120 mg. In one embodiment, the unit dose is about 50 mg. In one embodiment, the unit dose is about 55 mg. In one embodiment, the unit dose is 60 mg. In one embodiment, the unit dose is about 65 mg. In one embodiment, the unit dose is about 70 mg. In one embodiment, the unit dose is about 75 mg. In one embodiment, the unit dose is about 80 mg. In one embodiment, the unit dose is about 85 mg. In one embodiment, the unit dose is about 90 mg. In one embodiment, the unit dose is about 95 mg. In one embodiment, the unit dose is about 100 mg. In one embodiment, the unit dose is 105 mg. In one embodiment, the unit dose is about 110 mg. In one embodiment, the unit dose is about 115 mg. In one embodiment, the unit dose is about 120 mg.

In some embodiments, the at least one additional dose of noribogaine, noribogaine derivative, or pharmaceutically acceptable salt or solvate thereof is from 5 mg to 75 mg. In one embodiment, the unit dose is 5 mg. In one embodiment, the unit dose is 10 mg. In one embodiment, the unit dose is 15 mg. In one embodiment, the unit dose is 20 mg. In one embodiment, the unit dose is 25 mg. In one embodiment, the unit dose is 30 mg. In one embodiment, the unit dose is 35 mg. In one embodiment, the unit dose is 40 mg. In one embodiment, the unit dose is 45 mg. In one embodiment, the unit dose is 50 mg. In one embodiment, the unit dose is 55 mg. In one embodiment, the unit dose is 60 mg. In one embodiment, the unit dose is 65 mg. In one embodiment, the unit dose is 70 mg. In one embodiment, the unit dose is 75 mg.

In some embodiments, the formulation comprises a delivery vehicle, as described above. In one embodiment, the delivery vehicle comprises 5 mg to 120 mg noribogaine, noribogaine derivative, or pharmaceutically acceptable salt or solvate thereof.

In some embodiments, the formulation is a controlled release formulation. The term "controlled release formulation" includes sustained release and time-release formulations. Controlled release formulations are well-known in the art. These include excipients that allow for sustained, periodic, pulse, or delayed release of the drug. Controlled release formulations include, without limitation, embedding of the drug into a matrix; enteric coatings; microencapsulation; gels and hydrogels; implants; transdermal patches; and any other formulation that allows for controlled release of a drug.

In one embodiment, the amount of noribogaine is sufficient to provide an average serum concentration of noribogaine from about 50 ng/mL to about 180 ng/mL, or about 60 ng/mL to about 180 ng/mL. In one embodiment, the amount of noribogaine is sufficient to provide an average serum concentration of noribogaine from about 50 ng/mL to about 150 ng/mL, or about 60 ng/mL to about 150 ng/mL. In one embodiment, the amount of noribogaine is sufficient to provide an average serum concentration of noribogaine from about 50 ng/mL to about 120 ng/mL, or about 60 ng/mL to about 120 ng/mL. In one embodiment, the amount of noribogaine is sufficient to provide an average serum concentration of noribogaine from about 50 ng/mL to about 100 ng/mL, or about 60 ng/mL to about 100 ng/mL. In one embodiment, the amount of noribogaine is sufficient to provide an average serum concentration of noribogaine from about 80 ng/mL to about 100 ng/mL. The ranges include both extremes as well as any subranges between.

In some embodiments, the unit dose of noribogaine, noribogaine derivative, or pharmaceutically acceptable salt or solvate thereof is from about 20 mg to about 120 mg. In one embodiment, the unit dose is about 20 mg. In one embodiment, the unit dose is about 30 mg. In one embodiment, the unit dose is about 40 mg. In one embodiment, the unit dose is about 50 mg. In one embodiment, the unit dose is about 60 mg. In one embodiment, the unit dose is about 70 mg. In one embodiment, the unit dose is about 80 mg. In one embodiment, the unit dose is about 90 mg. In one embodiment, the unit dose is about 100 mg. In one embodiment, the unit dose is about 110 mg. In one embodiment, the unit dose is about 120 mg.

This invention further relates to pharmaceutically acceptable formulations comprising a unit dose of noribogaine, noribogaine derivative, or pharmaceutically acceptable salt and/or solvate thereof, wherein the amount of noribogaine is sufficient to provide an average serum concentration of about 50 ng/mL to about 850 ng/mL when administered to a patient. In a preferred embodiment, the amount of noribogaine is sufficient to provide an average serum concentration of about 50 ng/mL to about 400 ng/mL when administered to a patient.

In one embodiment, the amount of noribogaine is sufficient to provide an average serum concentration of noribogaine from about 50 ng/mL to about 800 ng/mL or about 60 ng/mL to about 800 ng/mL. In one embodiment, the amount of noribogaine is sufficient to provide an average serum concentration of noribogaine from about 50 ng/mL to about 700 ng/mL or about 60 ng/mL to about 700 ng/mL. In one embodiment, the amount of noribogaine is sufficient to provide an average serum concentration of noribogaine from about 50 ng/mL to about 600 ng/mL, or about 60 ng/mL to about 600 ng/mL. In a preferred embodiment, the amount of noribogaine is sufficient to provide an average serum concentration of noribogaine from about 50 ng/mL to about 500 ng/mL, or about 60 ng/mL to about 500 ng/mL. In one embodiment, the amount of noribogaine is sufficient to provide an average serum concentration of noribogaine from about 50 ng/mL to about 400 ng/mL, or about 60 ng/mL to about 400 ng/mL. In one embodiment, the amount of noribogaine is sufficient to provide an average serum concentration of noribogaine from about 50 ng/mL to about 300 ng/mL, or about 60 ng/mL to about 300 ng/mL. In one embodiment, the amount of noribogaine is sufficient to provide an average serum concentration of noribogaine from about 50 ng/mL to about 200 ng/mL, or about 60 ng/mL to about 200 ng/mL. In one embodiment, the amount of noribogaine is sufficient to provide an average serum concentration of noribogaine from about 50 ng/mL to about 100 ng/mL, or about 60 ng/mL to about 100 ng/mL. The ranges include both extremes as well as any subranges between.

In some embodiments, the formulation is designed for periodic administration, such as once, twice, three times, four times or five times daily with noribogaine, noribogaine derivative, or a pharmaceutically acceptable salt or solvate thereof. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made a qualified clinician.

In some embodiments, the non-therapeutic or therapeutic noribogaine formulation designed for administration in accordance with the methods provide herein can be suitable for a variety of delivery modes including, without limitation, oral, transdermal, sublingual, buccal, intrapulmonary or intranasal delivery. Formulations suitable for internal, pulmonary, rectal, nasal, vaginal, lingual, intravenous, intraarterial, intramuscular, intraperitoneal, intracutaneous and subcutaneous routes may also be used. Possible formulations include tablets, capsules, pills, powders, aerosols, suppositories, parenterals, and oral liquids, including suspensions, solutions and emulsions. Sustained release dosage forms may also be used. All formulations may be prepared using methods that are standard in the art (see e.g., Remington's Pharmaceutical Sciences, 16th ed., A. Oslo editor, Easton Pa. 1980).

In a preferred embodiment, the non-therapeutic or therapeutic noribogaine formulation is designed for oral administration, which may conveniently be provided in tablet, caplet, sublingual, liquid or capsule form. In certain embodiments, the noribogaine is provided as noribogaine HCl, with dosages reported as the amount of free base noribogaine. In some embodiments, the noribogaine HCl is provided in hard gelatin capsules containing only noribogaine HCl with no excipients.

Noribogaine or a noribogaine derivative can also be used in conjunction with any of the vehicles and excipients commonly employed in pharmaceutical preparations, e.g., talc, gum Arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing noribogaine may be prepared using conventional techniques that may include sterile isotonic saline, water, 1,3-butanediol, ethanol, 1,2-propylene glycol, polyglycols mixed with water, Ringer's solution, etc.

The compositions utilized herein may be formulated for aerosol administration, particularly to the respiratory tract and including intrapulmonary or intranasal administration. The compound will generally have a small particle size, for example of the order of 5 microns or less. Such a particle size may be obtained by means known in the art, for example by micronization. The active ingredient may be provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gases. The aerosol may conveniently also contain a surfactant such as lecithin. The dose of drug may be controlled by a metered valve. Alternatively, the active ingredients may be provided in the form of a dry powder, for example a powder mix of the compound in a suitable powder base such as lactose, starch, starch derivatives such as hydroxypropylmethyl cellulose and polyvinylpyrrolidine. In some embodiments, the powder carrier will form a gel in the nasal cavity. The powder composition may be presented in unit dose form, for example in capsules or cartridges, gelatin or blister packs, from which the powder may be administered by means of an inhaler.

The compositions utilized herein may be formulated for sublingual administration, for example as sublingual tablets. Sublingual tablets are designed to dissolve very rapidly. The formulations of these tablets contain, in addition to the drug, a limited number of soluble excipients, usually lactose and powdered sucrose, but sometimes dextrose and mannitol.

It has been discovered that noribogaine has a bitter taste to at least some patients. Accordingly, compositions for oral use (including sublingual, inhaled, and other oral formulations) may be formulated to utilize taste-masking technologies. A number of ways to mask the taste of bitter drugs are known in the art, including addition of sugars, flavors, sweeteners, or coatings; use of lipoproteins, vesicles, and/or liposomes; granulation; microencapsulation; numbing of taste buds; multiple emulsion; modification of viscosity; prodrug or salt formation; inclusion or molecular complexes; ion exchange resins; and solid dispersion. Any method of masking the bitterness of the compound of the invention may be used.

EXAMPLES

The following Examples are intended to further illustrate certain embodiments of the disclosure and are not intended to limit its scope.

Example 1

Pharmacokinetics and Pharmacodynamics of Noribogaine in Humans

Thirty-six healthy, drug-free male volunteers, aged between 18-55 years, were enrolled in and completed the study. This was an ascending single-dose, placebo-controlled, randomized double blind, parallel group study. Mean (SD) age was 22.0 (3.3) years, mean (SD) height was 1.82 (0.08) m, and mean (SD) weight was 78.0 (9.2) kg. Twenty-six subjects were Caucasian, 3 were Asian, 1 Maori, 1 Pacific Islander, and 5 Other. The protocol for this study was approved by the Lower South Regional Ethics Committee (LRS/12/06/015), and the study was registered with the Australian New Zealand Clinical Trial Registry (ACTRN12612000821897). All subjects provided signed informed consent prior to enrolment, and were assessed as suitable to participate based on review of medical history, physical examination, safety laboratory tests, vital signs and ECG.

Within each dose level, 6 participants were randomized to receive noribogaine and 3 to receive placebo, based on a computer-generated random code. Dosing began with the lowest noribogaine dose, and subsequent cohorts received the next highest dose after the safety, tolerability, and blinded pharmacokinetics of the completed cohort were reviewed and dose-escalation approved by an independent Data Safety Monitoring Board. Blinded study drug was administered as a capsule with 240 ml of water after an overnight fast of at least 10 hours. Participants did not receive any food until at least 5 hours post-dose. Participants were confined to the study site from 12 hours prior to drug administration, until 72 hours post-dose, and there were subsequent outpatient assessments until 216 hours post-dose.

Blood was obtained for pharmacokinetic assessments pre-dose and then at 0.25, 0.5, 0.75, 1.0, 1.25, 1.5, 2, 2.5, 3, 3.5, 4, 4.5, 5, 5.5, 6, 7, 8, 10, 12, 14, 18, 24, 30, 36, 48, 60, 72, 96, 120, 168 and 216 hours post-dose. Samples were centrifuged and plasma stored at −70° C. until analyzed. Block 24 hour urine collections were obtained following study drug administration for the 30 and 60 mg cohorts. Aliquots were frozen at −20° C. until analyzed.

Pulse oximetry and capnography data were collected continuously using a GE Carescape B650 monitoring system from 2 hours prior to dosing and until six hours after dosing, and thereafter at 12, 24, 48 and 72 hours post-dosing. Additional oximetry data were collected at 120, 168 and 216 hours. Pupillary miosis was assessed by pupillometry. Dark-adapted pupil diameter was measured in triplicate using a Neuroptics PLR-200 pupillometer under standardized light intensity (<5 lux) pre-dose, and at 2, 4, 6, 12, 24, 48, 72, 96, 120, 168 and 216 hours post-dosing.

Plasma noribogaine concentrations were determined in the 3 mg and 10 mg dose groups using a validated, sensitive LCMSMS method. Sample preparation involved double extraction of basified plasma samples with tert-butyl methyl ether, drying the samples under a stream of nitrogen and reconstitution of sample with acetonitrile:B.P. water (5:95, v/v) containing 0.1% (v/v) formic acid. The compounds were separated by a 150×2.0 mm Luna 5 μm C18 column and detected with a triple-quadruple API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, and for the internal standard noribogaine-$d_4$ m/z 301.1→122.2. Analyst® software was used for data acquisition and processing. The ratio of the peak area of noribogaine to the internal standard noribogaine-$d_4$ was used for calibration and measurement of the unknown concentration of noribogaine. The lower limit of quantification (LLOQ) was 0.025 ng/ml noribogaine. The calibration curve was between 0.025 and 25.600 ng/ml noribogaine. Mobile phase A was acetonitrile:B.P. water (5:95, v/v) containing 0.1% (v/v) formic acid, and mobile phase B was acetonitrile:B.P. water (95:5, v/v) containing 0.1% (v/v) formic acid. Total run time was 6 minutes. Binary flow: Initial concentration was 8% mobile phase B; hold at 8% mobile phase B for 0.5 minutes and linear rise to 90% mobile phase B over 1.5 minutes; hold at 90% mobile phase B for 1 minute and then drop back to 8% mobile phase B over 0.01 minute. Equilibrate system for 3 minutes. Total run time was 6 minutes. Within- and between-day assay precision was <9%, and within- and between-day assay accuracy was <9%.

Plasma noribogaine concentrations were determined in the 30 mg and 60 mg dose groups using a validated, sensitive LCMSMS method. Sample preparation involved deproteinization of plasma samples with acetonitrile and dilution of sample with 0.1% (v/v) formic acid. The compounds were separated by a 150×2.0 mm Luna 5 µm C18 column and detected with a triple-quadruple API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, and for the internal standard noribogaine-$d_4$ m/z 301.1→122.2. Analyst® software was used for data acquisition and processing. The ratio of the peak area of noribogaine to the internal standard noribogaine-$d_4$ was used for calibration and measurement of the unknown concentration of noribogaine. The LLOQ was 0.50 ng/ml noribogaine. The calibration curve was between 0.50 and 256.00 ng/ml noribogaine. Mobile phase was the same as method A, and binary flow was also the same as method A. The within- and between-day assay precision was <9%, and the within- and between-day assay accuracy was <9%.

Plasma noribogaine glucuronide concentrations were determined in the 30 mg and 60 mg dose groups using a validated sensitive LCMSMS method. Sample preparation involved deproteinization of plasma samples with acetonitrile, drying the samples under a stream of nitrogen and reconstitution of sample with acetonitrile:B.P. water (5:95, v/v) containing 0.1% (v/v) formic acid. The compounds were separated by a 150×2.0 mm Luna 5 µm C18 column and detected with a triple-quadruple API 4000 or 5000 mass spectrometer using electrospray ionization in positive mode and multiple reaction monitoring. Noribogaine-$d_4$ was used as the internal standard. The precursor-product ion transition values for noribogaine glucuronide were m/z 472.8→297.3, and for the internal standard noribogaine-$d_4$ m/z 301.1→122.2. Analyst® software was used for data acquisition and processing. The ratio of the peak area of noribogaine glucuronide to the internal standard noribogaine-$d_4$ was used for calibration and measurement of the unknown concentration of noribogaine glucuronide. The LLOQ was 0.050 ng/ml noribogaine glucuronide. The calibration curve was between 0.050 and 6.400 ng/ml noribogaine glucuronide. Mobile phases was the same as method A. Binary flow: Initial concentration was 6% mobile phase B; hold at 6% mobile phase B for 0.5 minutes and linear rise to 90% mobile phase B over 2 minutes; hold at 90% mobile phase B for 1 minute and then drop back to 6% mobile phase B over 0.01 minute. Equilibrate system for 3.5 minutes. Total run time was 7 minutes. The within- and between-day assay precision was <11%, and the within- and between-day assay accuracy was <10%.

Urine noribogaine and noribogaine glucuronide concentrations were determined in the 30 mg and 60 mg dose groups using a validated sensitive LCMSMS method. Sample preparation involved deproteinization of urine samples with acetonitrile and dilution of the sample with 0.1% (v/v) formic acid. The compounds were separated by a 150×2.0 mm Luna 5 µm C18 column and detected with a triple-quadruple API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, noribogaine glucuronide m/z 472.8→297.3, and for the internal standard noribogaine-$d_4$ m/z 301.1→122.2. Analyst® software was used for data acquisition and processing. The ratios of the peak area of noribogaine and noribogaine glucuronide to the internal standard noribogaine-$d_4$ were used for calibration and measurement of the unknown concentration of noribogaine and its glucuronide. Assay LLOQ was 20.0 ng/ml for noribogaine and 2.0 ng/ml for noribogaine glucuronide. The calibration curve was between 20.0 and 5120.0 ng/ml noribogaine, and 2.0 and 512.0 ng/ml noribogaine glucuronide. Mobile phases were as described in method A, and binary flow as in method C. The within- and between-day assay precision was <13%, and within- and between-day assay accuracy was <12%.

Noribogaine and noribogaine glucuronide concentrations above the limit of quantification were used to calculate pharmacokinetic parameters using model-independent methods. The maximum plasma concentration (Cmax) and time to maximum plasma concentration (Tmax) were the observed values. Plasma concentration data in the post-distribution phase of the plasma concentration-time plot were fitted using linear regression to the formula ln C=ln Co−t.Kel, where Co was the zero-time intercept of the extrapolated terminal phase and Kel was the terminal elimination rate constant. The half-life ($t_{1/2}$) was determined using the formula $t_{1/2}$=0.693/Kel. The area under the concentration-time curve (AUC) from time zero to the last determined concentration-time point (tf) in the post distribution phase was calculated using the trapezoidal rule. The area under the curve from the last concentration-time point in the post distribution phase (Ctf) to time infinity was calculated from $AUC_{t-\infty}$=Ctf/Kel. The concentration used for Ctf was the last determined value above the LLOQ at the time point. The total $AUC_{0-\infty}$ was obtained by adding $AUC_{tf}$ and $AUC_{t-\infty}$. Noribogaine apparent clearance (CL/F) was determined using the formula CL/F=Dose/$AUC_{0-\infty}$×1000, and apparent volume of distribution (Vd/F) was determined using the formula Vd/F=(CL/F)/Kel. Total urine noribogaine was the sum of both analytes.

Summary statistics (means, standard deviations, and coefficients of variation) were determined for each dose group for safety laboratory test data, ECG and pharmacokinetic parameters, and pharmacodynamic variables. Categorical variables were analysed using counts and percentages. Dose-proportionality of AUC and Cmax was assessed using linear regression. The effect of dose on pharmacodynamic parameter values over time was assessed using two-factor analysis of variance (ANOVA). Pairwise comparisons (with Tukey-Kramer adjustment) between each dose group to the placebo were conducted at each time point using the least squares estimates obtained from the ANOVA, using SAS Proc Mixed (SAS ver 6.0).

Results

Pharmacokinetics: Mean plasma concentration-time plots of noribogaine are shown in FIG. 1, and mean pharmacokinetic parameters are shown in Table 1.

TABLE 1

| | 3 mg (n = 6) (mean (SD)) | 10 mg (n = 6) (mean (SD)) | 30 mg (n = 6) (mean (SD)) | 60 mg (n = 6) (mean (SD) |
|---|---|---|---|---|
| | Noribogaine | | | |
| $AUC_{0-\infty}$ (ng · hr/ml) | 74.2 (13.1) | 254.5 (78.9) | 700.4 (223.3) | 1962.2 (726.5) |

TABLE 1-continued

|  | 3 mg (n = 6) (mean (SD)) | 10 mg (n = 6) (mean (SD)) | 30 mg (n = 6) (mean (SD)) | 60 mg (n = 6) (mean (SD) |
|---|---|---|---|---|
| $AUC_{0-216}$ (ng · hr/ml) | 72.2 (13.2) | 251.4 (78.5) | 677.6 (221.1) | 1935.4 (725.4) |
| Cmax (ng/ml) | 5.2 (1.4) | 14.5 (2.1) | 55.9 (14.8) | 116.0 (22.5) |
| Tmax (hr) | 1.9 (0.6) | 2.9 (1.8) | 1.8 (0.6) | 2.4 (0.6) |
| $t_{1/2}$ (hr) | 40.9 (8.7) | 49.2 (11.5) | 27.6 (7.0)) | 29.1 (9.3) |
| Vd/F (L) | 2485.1 (801.5) | 3085.8 (1197.0) | 1850.8 (707.9) | 1416.8 (670.1) |
| CL/F (L/h) | 41.4 (7.0) | 42.3 (12.0) | 46.9 (16.4) | 34.0 (11.4) |
| Noribogaine glucuronide | | | | |
| $AUC_{0-\infty}$ (ng · hr/ml) | — | — | 25.8 (9.3) | 67.1 (21.9) |
| $AUC_{0-216}$ (ng · hr/ml) | — | — | 25.7 (9.1) | 65.0 (21.5) |
| Cmax (ng/ml) | — | — | 1.8 (0.6) | 4.1 (1.2) |
| Tmax (hr) | — | — | 3.0 (0.6) | 3.8 (1.2) |
| $t_{1/2}$ (hr) | — | — | 20.6 (4.9) | 23.1 (3.0) |

Noribogaine was rapidly absorbed, with peak concentrations occurring 2-3 hours after oral dosing. Fluctuations in individual distribution-phase concentration-time profiles may suggest the possibility of enterohepatic recirculation (see highlighted individual 4-8 hour profiles in FIG. 1, insert). Both Cmax and AUC increased linearly with dose (Table 1, upper panel). Mean half-life estimates of 28-50 hours were observed across dose groups for noribogaine. Volume of distribution was extensive (1417-3086 L across dose groups).

Figure 2:
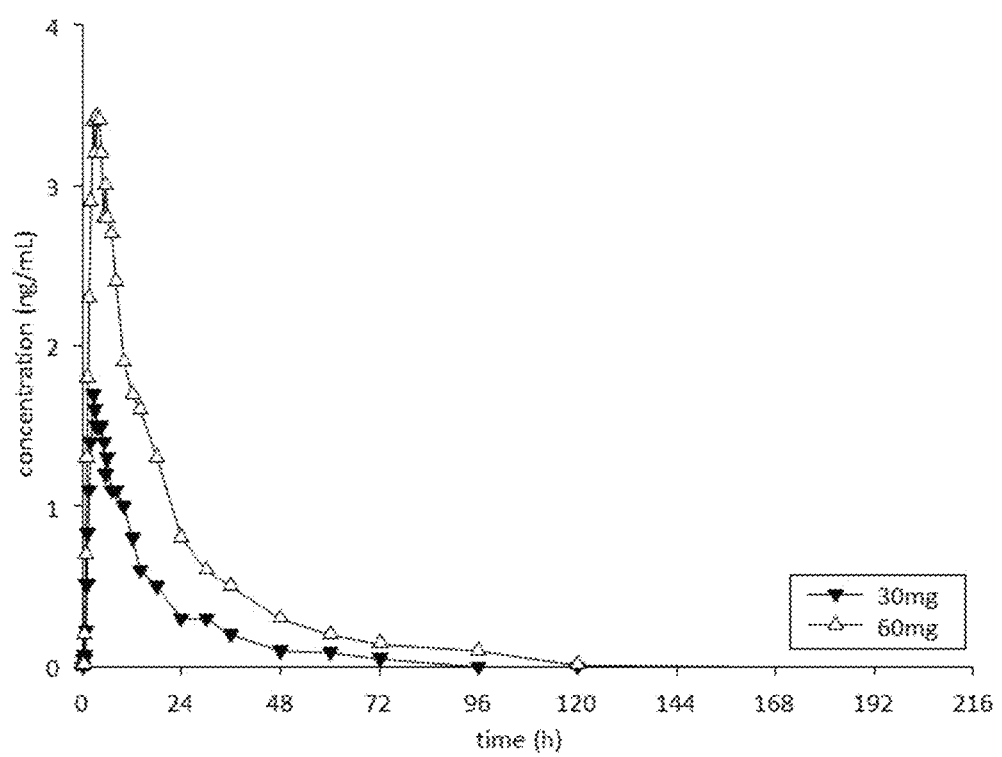
FIG. 2 represents mean plasma noribogaine glucuronide concentration-time profiles in healthy patients after single oral 30 or 60 mg doses.

Mean plasma noribogaine glucuronide concentration-time plots for the 30 mg and 60 mg dose group are shown in FIG. 2, and mean pharmacokinetic parameters are shown in Table 1, lower panel. Noribogaine glucuronide was detected in all subjects by 0.75 hours, with peak concentrations occurring 3-4 hours after noribogaine dosing. Mean half-life of 21-23 hours was estimated for plasma noribogaine glucuronide. The proportion of noribogaine glucuronide Cmax and AUC relative to noribogaine was 3-4% for both dose groups. Total urine noribogaine elimination was 1.16 mg and 0.82 mg for the 30 mg and 60 mg dose groups respectively, representing 3.9% and 1.4% of the doses administered.

The subject mean serum levels over time of noribogaine free base from a single dose of 3 mg noribogaine free base under fasting conditions were plotted. The mean $C_{max}$ of 5.2 ng/ml was observed 1.9 hours after administration, while the mean AUC/24 hr of 3.1 ng/ml was obtained.

The subject mean serum levels over time of noribogaine free base from a single dose of 10 mg noribogaine free base under fasting conditions were plotted. The mean $C_{max}$ of 14.5 ng/ml was observed 2.9 hours after administration, while the mean AUC/24 hr of 10.6 ng/ml was obtained.

The subject mean serum levels over time of noribogaine free base from a single dose of 30 mg noribogaine free base under fasting conditions were plotted. The mean $C_{max}$ of 55.9 ng/ml was observed between 1.75 hours after administration, while the mean AUC/24 of 29.2 ng/ml was obtained.

The subject mean serum levels over time of noribogaine free base from a single dose of 60 mg noribogaine free base under fasting conditions were plotted. The mean $C_{max}$ of 116 ng/ml was observed between 1.75 hours after administration, while the mean AUC/24 ng/ml of 61 was obtained.

The subject mean serum levels over time of noribogaine free base for all 4 cohorts were plotted. The extrapolated dosage of noribogaine free base required to provide a $C_{max}$ ranging from about 5.2 ng/ml to about 1980 ng/ml and an AUC/24 hr of about 3.1 ng/ml to about 1100 ng/ml was determined.

Pharmacodynamics: There was no evidence of pupillary constriction in subjects dosed with noribogaine. No between-dose group differences in pupil diameter were detected over time. After adjusting for baseline differences, comparison of each dose group with placebo by ANOVA showed no statistically significant differences (p>0.9).

Noribogaine treatment showed no analgesic effect in the cold pressor test. Analgesic effect was assessed based on duration of hand immersion in ice water and on visual analog scale (VAS) pain scores upon hand removal from the water bath. For duration of hand immersion, after adjusting for baseline differences, comparison of each dose group with placebo by ANOVA showed no statistically significant differences (p>0.9). Similarly, for VAS pain scores, after adjusting for baseline differences, comparison of each dose group with placebo by ANOVA showed no statistically significant differences (p=0.17).

Pharmacodynamics: There was no evidence of pupillary constriction in subjects dosed with noribogaine. No between-dose group differences in pupil diameter were detected over time. After adjusting for baseline differences, comparison of each dose group with placebo by ANOVA showed no statistically significant differences (p>0.9).

Noribogaine treatment showed no analgesic effect in the cold pressor test. Analgesic effect was assessed based on duration of hand immersion in ice water and on visual analog scale (VAS) pain scores upon hand removal from the water bath. For duration of hand immersion, after adjusting for baseline differences, comparison of each dose group with placebo by ANOVA showed no statistically significant differences (p>0.9). Similarly, for VAS pain scores, after adjusting for baseline differences, comparison of each dose group with placebo by ANOVA showed no statistically significant differences (p=0.17).

Example 2

Safety and Tolerability of Noribogaine in Healthy Humans

Safety and tolerability of noribogaine were tested in the group of volunteers from Example 1. Cold pressor testing was conducted in 1° C. water according to the method of Mitchell et al. (*J Pain* 5:233-237, 2004) pre-dose, 6, 24, 48, 72 and 216 hours post-dosing. Safety evaluations included clinical monitoring, recording of adverse events (AEs), safety laboratory tests, vital signs, ECG telemetry from −2 h to 6 h after dosing, and 12-lead electrocardiograms (ECGs) up to 216 hours post-dosing.

Results

A total of thirteen adverse events were reported by seven participants (Table 2). Six adverse events were reported by three participants in the placebo group, five adverse events were reported by two subjects in the 3 mg dose group, and one adverse event was reported by single subjects in the 10 mg and 30 mg dose groups, respectively. The most common adverse events were headache (four reports) and epistaxis (two reports). All adverse events were of mild-moderate intensity, and all resolved prior to study completion. There were no changes in vital signs or safety laboratory tests of note. In particular, there were no changes in oximetry or capnography, or changes in respiratory rate. There were no QTcF values >500 msec at any time. One subject dosed with 10 mg noribogaine had a single increase in QTcF of >60 msec at 24 hours post-dosing.

TABLE 2

| Dose (mg) | Mild | Moderate | Severe |
|---|---|---|---|
| Placebo | Blepharitis | Epistaxis | — |
| | Bruising | | |
| | Dry Skin | | |
| | Eye pain, nonspecific | | |
| | Infection at cannula site | | |
| 3 | Back pain | Headache | — |
| | Dizziness | | |
| | Epistaxis | | |
| | Headache | | |
| 10 | Headache | — | — |
| 30 | Headache | — | — |
| 60 | — | — | — |

Example 3

Safety, Tolerability, and Efficacy of Noribogaine in Opioid-Addicted Humans

This example is to illustrate that noribogaine can be administered at a therapeutic dosing while maintaining an acceptable QT interval. While the therapy employed is directed to opioid-dependent participants in a randomized, placebo-controlled, double-blind trial, the results show that a therapeutic window can be established for noribogaine.

The efficacy of noribogaine in humans was evaluated in opioid-dependent participants in a randomized, placebo-controlled, double-blind trial. Patients had been receiving methadone treatment as the opioid substitution therapy, but were transferred to morphine treatment prior to noribogaine administration. This was done to avoid negative noribogaine-methadone interactions that are not observed between noribogaine and morphine. See U.S. application Ser. No. 14/214,157, filed Mar. 14, 2014 and Ser. No. 14/346,655, filed Mar. 21, 2014, which are incorporated herein by reference in their entireties.

Three cohorts of nine (9) subjects (6 administered noribogaine and 3 administered placebo in each cohort) were evaluated for tolerability, pharmacokinetics, and efficacy. Cohort 1 received a single dose of 60 mg noribogaine or placebo. Cohort 2 received a single dose of 120 mg noribogaine or placebo. Cohort 3 received a single dose of 180 mg noribogaine or placebo. Treatment was administered 2 hours after last morphine dose and the time to resumption of morphine (opioid substitution treatment, OST) was determined. Few adverse effects of noribogaine were observed in any of the participants, including no hallucinatory effects. Table 3 shows the reported adverse events for each treatment that were not attributable to withdrawal from opioids. Headaches were frequent in the placebo and 60 mg noribogaine treatment groups, but were attenuated in the 120 mg and 180 mg dose groups.

TABLE 3

Treatment Emergent Adverse Events Summary

| System Organ Class Preferred Term | Placebo (N = 9) | 60 mg (N = 6) | 120 mg (N = 6) | 180 mg (N = 6) |
|---|---|---|---|---|
| Number of Subjects Reporting any AEs | 19:7 (77.8%) | 15:5 (83.3%) | 28:6 (100.0%) | 17:4 (66.7%) |
| Ear and Labyrinth Disorders | 0 | 0 | 2:2 (33.3%) | 0 |
| Tinnitus | 0 | 0 | 2:2 (33.3%) | 0 |
| Eye Disorders | 2:2 (22.2%) | 3:3 (50.0%) | 5:5 (83.3%) | 5:4 (66.7%) |
| Visual Impairment | 2:2 (22.2%) | 2:2 (33.3%) | 5:5 (83.3%) | 5:4 (66.7%) |
| Dry Eye | 0 | 1:1 (16.7%) | 0 | 0 |
| Gastrointestinal Disorders | 3:2 (22.2%) | 2:2 (33.3%) | 7:2 (33.3%) | 4:2 (33.3%) |
| Nausea | 1:1 (11.1%) | 0 | 3:2 (33.3%) | 2:2 (33.3%) |
| Dry Mouth | 0 | 0 | 1:1 (16.7%) | 1:1 (16.7%) |
| Vomiting | 0 | 0 | 2:1 (16.7%) | 1:1 (16.7%) |
| Diarrhoea | 1:1 (11.1%) | 0 | 1:1 (16.7%) | 0 |
| Dyspepsia | 1:1 (11.1%) | 2:2 (33.3%) | 0 | 0 |
| General Disorders and Administration Site Conditions | 4:3 (33.3%) | 0 | 2:2 (33.3%) | 1:1 (16.7%) |
| Catheter Site Related Reaction | 0 | 0 | 0 | 1:1 (16.7%) |
| Catheter Site Pain | 3:2 (22.2%) | 0 | 2:2 (33.3%) | 0 |
| Malaise | 1:1 (11.1%) | 0 | 0 | 0 |
| Infections and Infestations | 1:1 (11.1%) | 0 | 1:1 (16.7%) | 2:2 (33.3%) |
| Cellulitis | 0 | 0 | 1:1 (16.7%) | 1:1 (16.7%) |
| Urinary Tract Infection | 0 | 0 | 0 | 1:1 (16.7%) |
| Catheter Site Infection | 1:1 (11.1%) | 0 | 0 | 0 |
| Musculoskeletal and Connective Tissue Disorders | 1:1 (11.1%) | 2:1 (16.7%) | 0 | 2:2 (33.3%) |
| Back Pain | 1:1 (11.1%) | 2:1 (16.7%) | 0 | 1:1 (16.7%) |
| Limb Discomfort | 0 | 0 | 0 | 1:1 (16.7%) |

TABLE 3-continued

Treatment Emergent Adverse Events Summary

| System Organ Class<br>Preferred Term | Placebo<br>(N = 9) | 60 mg<br>(N = 6) | 120 mg<br>(N = 6) | 180 mg<br>(N = 6) |
|---|---|---|---|---|
| Nervous System Disorders | 7:5 (55.6%) | 7:4 (66.7%) | 5:4 (66.7%) | 3:2 (33.3%) |
| Headache | 6:5 (55.6%) | 7:4 (66.7%) | 2:2 (33.3%) | 3:2 (33.3%) |
| Hyperaesthesia | 0 | 0 | 1:1 (16.7%) | 0 |
| Pseudoparalysis | 0 | 0 | 1:1 (16.7%) | 0 |
| Tremor | 0 | 0 | 1:1 (16.7%) | 0 |
| Somnoience | 1:1 (11.1%) | 0 | 0 | 0 |
| Psychiatric Disorders | 1:1 (11.1%) | 1:1 (16.7%) | 0 | 0 |
| Depressed Mood | 0 | 1:1 (16.7%) | 0 | 0 |
| Euphoric Mood | 1:1 (11.1%) | 0 | 0 | 0 |
| Respiratory, Thoracic and Mediastinal Disorders | 0 | 0 | 4:2 (33.3%) | 0 |
| Epistaxis | 0 | 0 | 2:1 (16.7%) | 0 |
| Oropharyngeal Pain | 0 | 0 | 1:1 (16.7%) | 0 |
| Rhinorrhoea | 0 | 0 | 1:1 (16.7%) | 0 |
| Skin and Subcutaneous Tissue Disorders | 0 | 0 | 2:1 (16.7%) | 0 |
| Skin Discomfort | 0 | 0 | 1:1 (16.7%) | 0 |
| Skin Irritation | 0 | 0 | 1:1 (16.7%) | 0 |

Note:
Within each system organ class, Preferred Terms are presented by descending incidence of descending dosages groups and then the placebo group.
Note:
N = number of subjects in the safety population.

Figure 3:
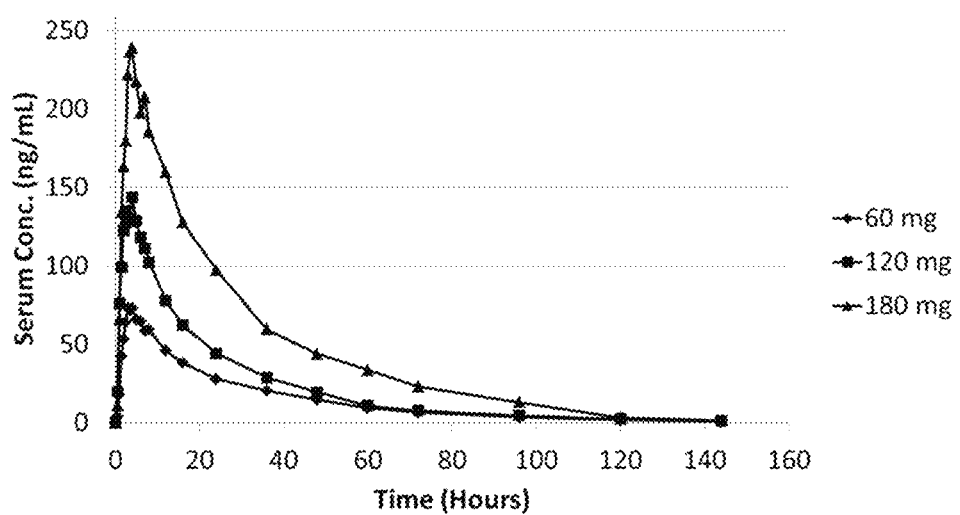
FIG. 3 illustrates the mean noribogaine concentration-time profile in opioid-addicted patients after a single oral 60 mg (diamonds), 120 mg (squares), or 180 mg (triangles) dose of noribogaine.

FIG. 3 indicates the average serum noribogaine concentration over time after administration of noribogaine for each cohort (60 mg, diamonds; 120 mg, squares; or 180 mg, triangles). Further results are detailed in U.S. Provisional Patent Application No. 62/023,100, filed Jul. 10, 2014, and titled "METHODS FOR ACUTE AND LONG-TERM TREATMENT OF DRUG ADDICTION," which is incorporated herein by reference in its entirety.

Results

Pharmacokinetic results for each cohort are given in Table 4. Maximum serum concentration of noribogaine (Cmax) increased in a dose-dependent manner. Time to Cmax (Tmax) was similar in all three cohorts. Mean half-life of serum noribogaine was similar to that observed in healthy patients.

a single 120 mg dose of noribogaine exhibited an average time to resumption of opioids of greater than 20 hours. Patients receiving a single 180 mg dose of noribogaine exhibited an average time to resumption of opioids similar to that of placebo. This demonstrates that increasing the dose of noribogaine to 180 mg results in a shorter time to resumption of OST than observed in patients receiving 120 mg noribogaine. Time to resumption of OST after treatment with 180 mg was still longer than untreated patients (7 hours, not shown) or those administered 60 mg noribogaine.

Patients were evaluated based on the Clinical Opiate Withdrawal Scale (COWS), Subjective Opiate Withdrawal Scale (SOWS), and Objective Opiate Withdrawal Scale (OOWS) scoring systems over the period of time between administration of noribogaine (or placebo) until resumption

TABLE 4

Pharmacokinetic results from the Patients in Phase IB Study

| PK parameter | Cohort 1 (60 mg)<br>Data (mean ± SD)<br>[range] | Cohort 2 (120 mg)<br>Data (mean ± SD)<br>[range] | Cohort 3 (180 mg)<br>Data (mean ± SD)<br>[range] |
|---|---|---|---|
| Cmax<br>(ng/ml) | 81.64 ± 23.77<br>[41.29-113.21] | 172.79 ± 30.73<br>[138.84-229.55] | 267.88 ± 46.92<br>[204.85-338.21] |
| Tmax<br>(hours) | 3.59 ± 0.92<br>[2.50-5.00] | 2.99 ± 1.23<br>[0.98-4.02] | 4.41 ± 1.80<br>[3.00-8.00] |
| $AUC_{(0-T)}$<br>(ng · hr/ml) | 2018.01 ± 613.91<br>[1094.46-2533.44] | 3226.38 ± 1544.26<br>[1559.37-5638.98] | 6523.28 ± 2909.80<br>[3716.69-10353.12] |
| $AUC_{(0-\infty)}$<br>(ng · hr/ml) | 2060.31 ± 609.39<br>[1122.29-2551.63] | 3280.50 ± 1581.43<br>[1595.84-5768.52] | 6887.67 ± 3488.91<br>[3734.21-12280.91] |
| Half-life<br>(hrs) | 29.32 ± 7.28<br>[18.26-37.33] | 30.45 ± 9.14<br>[21.85-48.33] | 23.94 ± 5.54<br>[19.32-34.90] |
| Vd/F | 1440.7 ± 854.0<br>[619.5-2772.5] | 2106.43 ± 1644.54<br>[824.24-5243.78] | 1032.19 ± 365.30<br>[581.18-1608.98] |
| Cl/F | 32.14 ± 12.38<br>[23.51-53.46] | 44.68 ± 21.40<br>[20.80-75.20] | 31.47 ± 13.12<br>[14.66-48.20] |

Figure 4:
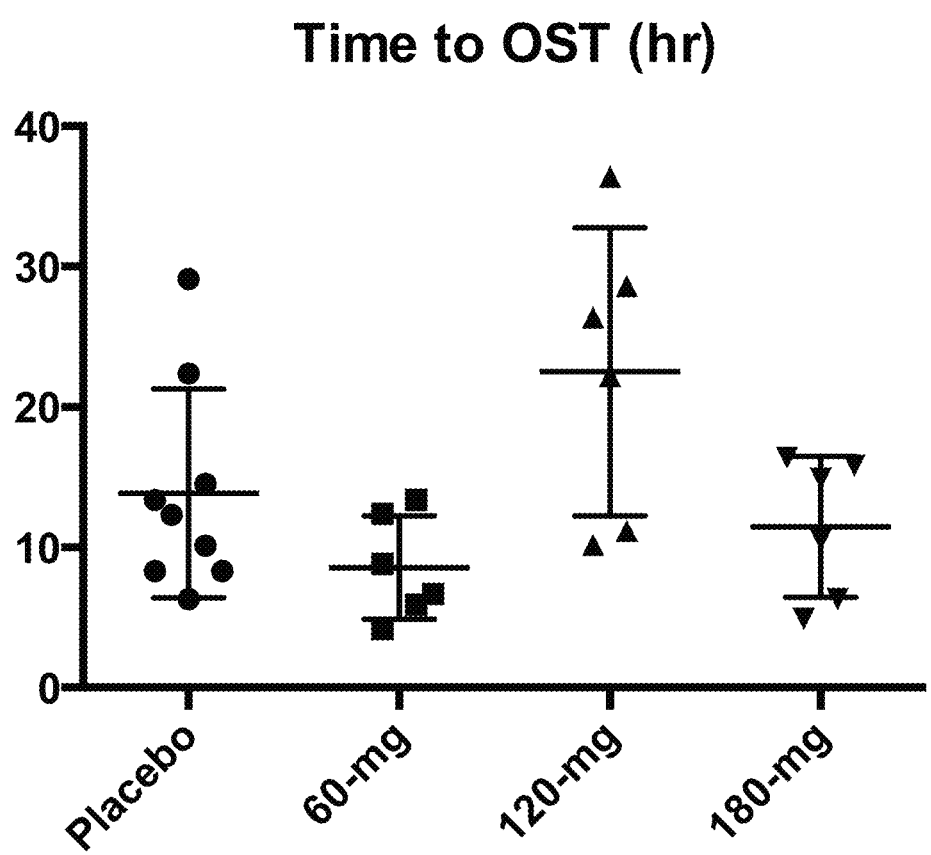
FIG. 4 illustrates hours to resumption of opioid substitution treatment (OST) for each patient given placebo (circles), or a single oral dose of noribogaine (60 mg, squares; 120 mg, triangles; 180 mg, inverted triangles). Center horizontal line represents mean. Error bars represent standard deviation.

FIG. 4 indicates the time to resumption of morphine (OST) for patients treated with placebo (circles), 60 mg noribogaine (squares), 120 mg noribogaine (triangles), and 180 mg noribogaine (inverted triangles). Patients receiving of OST. These scales are outlined in Guidelines for the Psychosocially Assisted Pharmacological Treatment of Opioid Dependence, World Health Organization, Geneva (2009), Annex 10, which is incorporated herein by reference in its entirety. The scales measure the intensity of withdrawal symptoms, based on clinical, subjective, and objective indicia.

Figure 5:
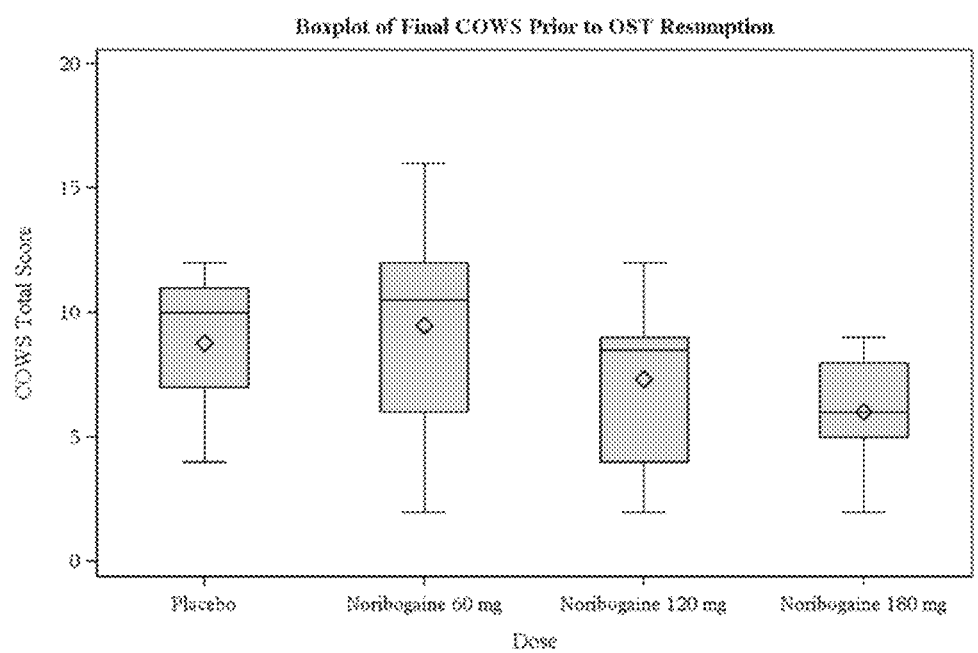
FIG. 5 illustrates results of noribogaine treatment on final COWS scores before resumption of OST. Boxes include values representing 25%-75% quartiles. Diamonds represent the median, crossbars represent mean. Whiskers represent values within one standard deviation of mid-quartiles. No outliers were present.

FIG. 5 shows the COWS scores at time of resumption of OST for each cohort. Box includes values representing 25%-75% quartiles. Diamond=median; crossbar in box=mean; whiskers=values within standard deviation of mid-quartiles. No outliers present. The highly variable COWS scores across and within each cohort indicates that patients were resuming opiates without relation to the intensity of withdrawal. This was also reflected in SOWS and OOWS scores at the time of resumption of OST.

Figure 6A:
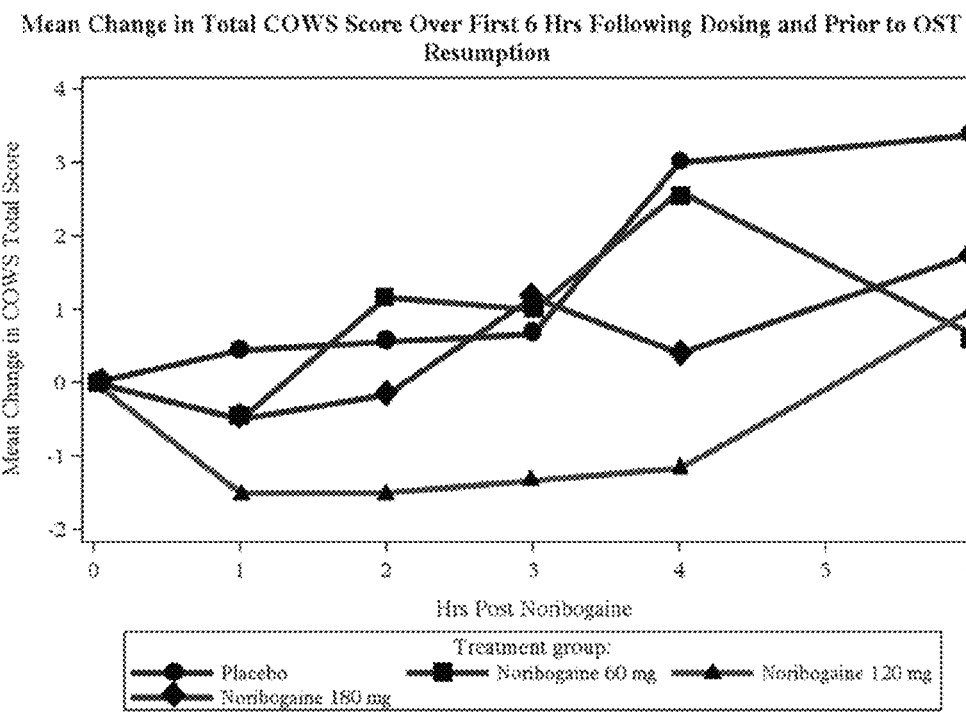
FIG. 6A illustrates of the mean change in total COWS scores over the first 6 hours following dosing of noribogaine (60 mg, squares; 120 mg, triangles; 180 mg, diamonds) or placebo (circles). Data is given relative to baseline COWS score.
Figure 6B:
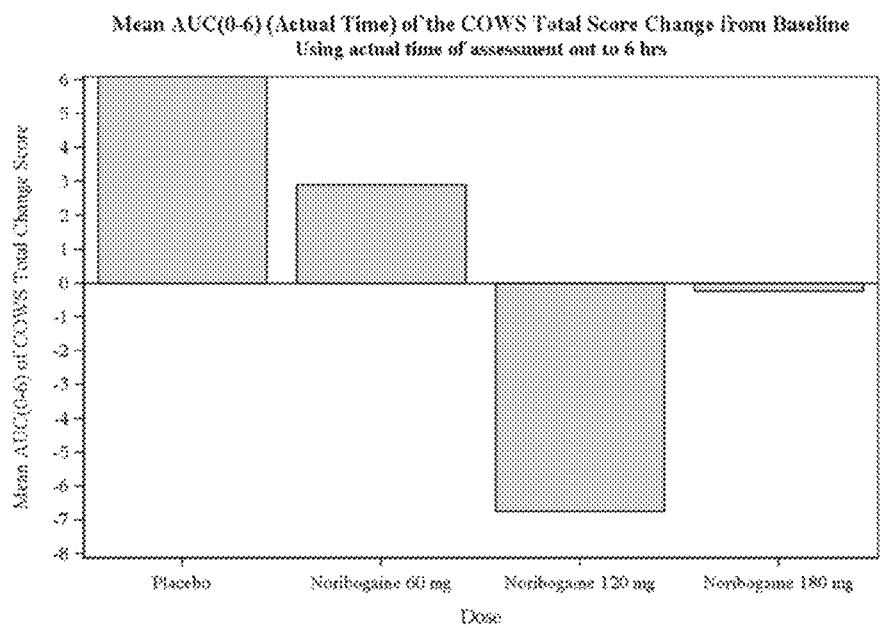
FIG. 6B illustrates the mean area under the curve (AUC) over the initial 6 hour period after administration of noribogaine or placebo, based on the COWS score data given in FIG. 6A. A negative change in score indicates that withdrawal symptoms subsided over the period.
Figure 7A:
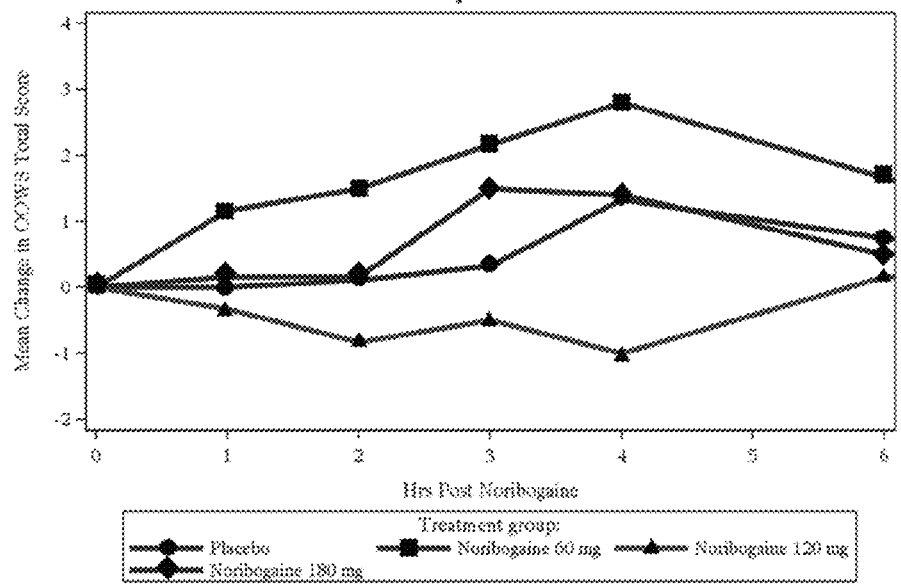
FIG. 7A illustrates of the mean change in total OOWS scores over the first 6 hours following dosing of noribogaine (60 mg, squares; 120 mg, triangles; 180 mg, diamonds) or placebo (circles). Data is given relative to baseline OOWS score.
Figure 7B:
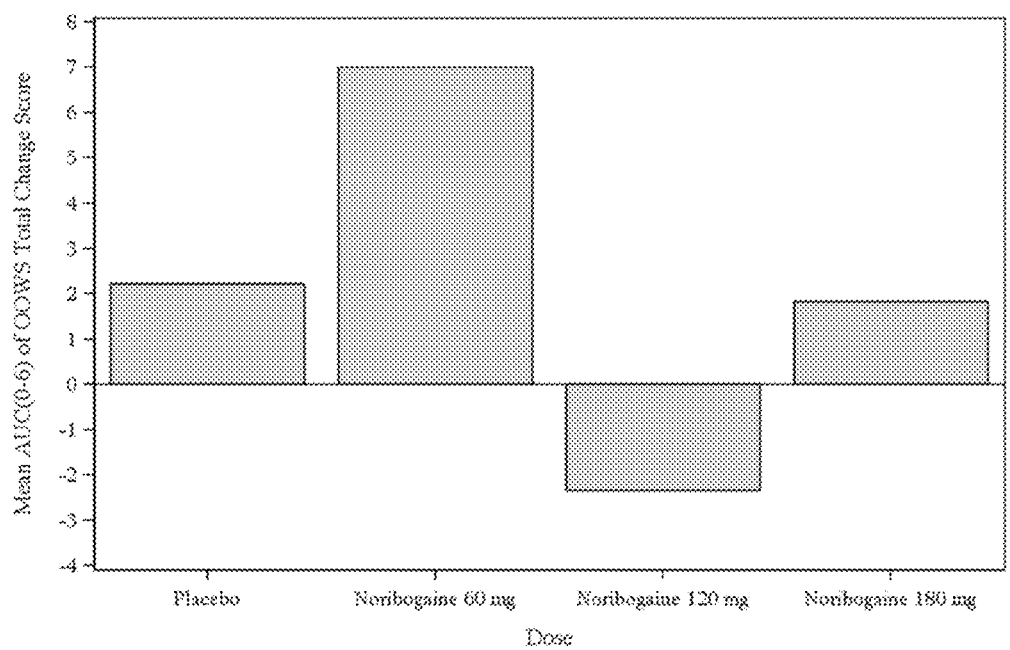
FIG. 7B illustrates the mean area under the curve (AUC) over the initial 6 hour period after administration of noribogaine or placebo, based on the OOWS score data given in FIG. 7A. A negative change in score indicates that withdrawal symptoms subsided over the period.
Figure 8A:
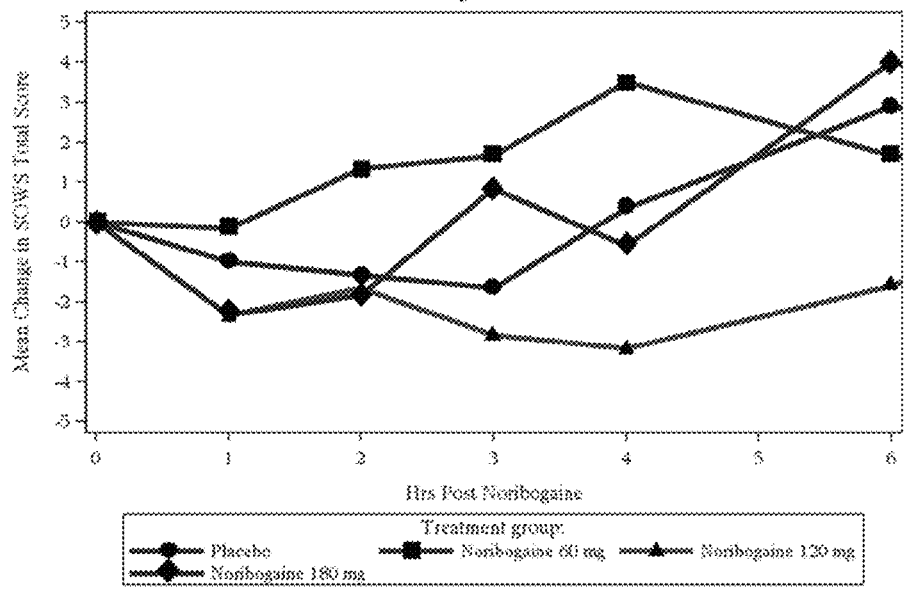
FIG. 8A illustrates of the mean change in total SOWS scores over the first 6 hours following dosing of noribogaine (60 mg, squares; 120 mg, triangles; 180 mg, diamonds) or placebo (circles). Data is given relative to baseline SOWS score.
Figure 8B:
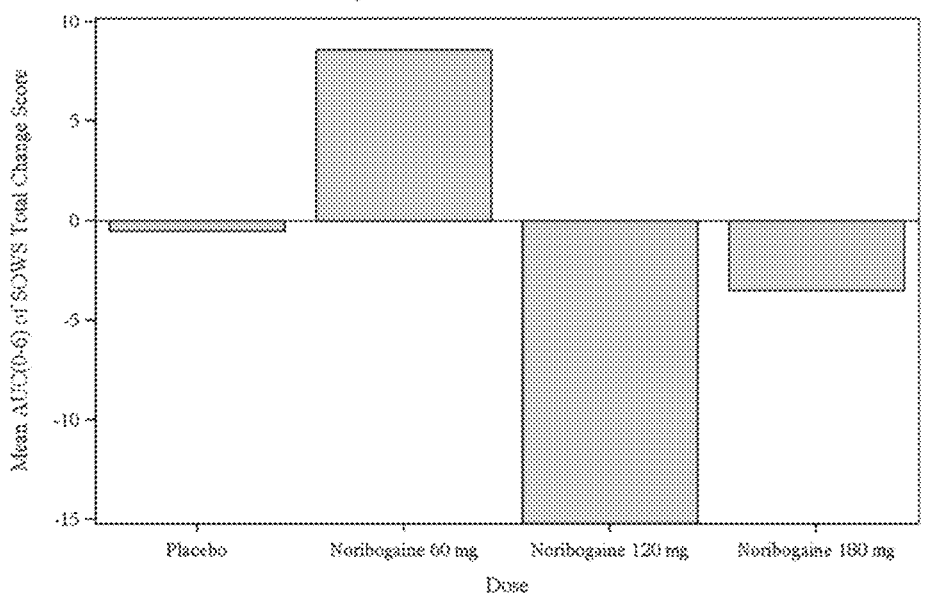
FIG. 8B illustrates the mean area under the curve (AUC) over the initial 6 hour period after administration of noribogaine or placebo, based on the SOWS score data given in FIG. 8A. A negative change in score indicates that withdrawal symptoms subsided over the period.

FIG. 6A shows the mean change in total COWS scores over the first six hours following dosing and prior to resumption of OST. FIG. 6B shows the mean AUC(0-6 hours) of the COWS total score change from baseline. FIG. 7A shows the mean change in total OOWS scores over the first six hours following dosing and prior to resumption of OST. FIG. 7B shows the mean AUC(0-6 hours) of the OOWS total score change from baseline. FIG. 8A shows the mean change in total SOWS scores over the first six hours following dosing and prior to resumption of OST. FIG. 8B shows the mean AUC(0-6 hours) of the SOWS total score change from baseline. These data indicate that withdrawal symptoms get worse over time after cessation of OST, and that patients administered placebo experience generally worse withdrawal symptoms over that period. Patients who received 120 mg noribogaine generally experienced fewer withdrawal symptoms than the other patients, regardless of the scale used. Patients administered placebo generally experienced more withdrawal symptoms than patients who were administered noribogaine.

Figure 9A:
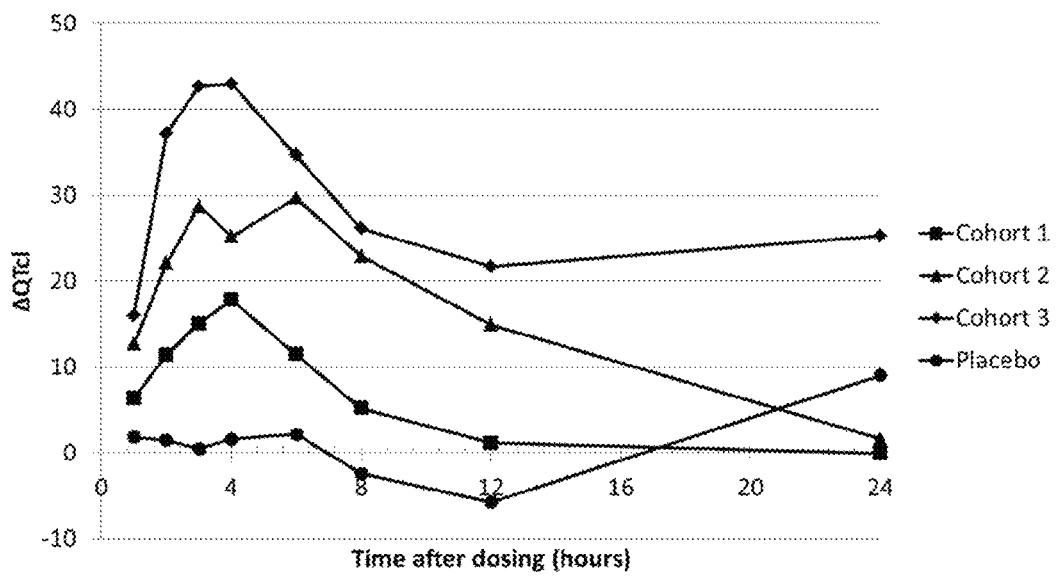
FIG. 9A illustrates the average change in QT interval ($\Delta$QTcl) for each cohort (60 mg, squares; 120 mg, triangles; 180 mg, diamonds) or placebo (circles) over the first 24 hours post administration.
Figure 9B:
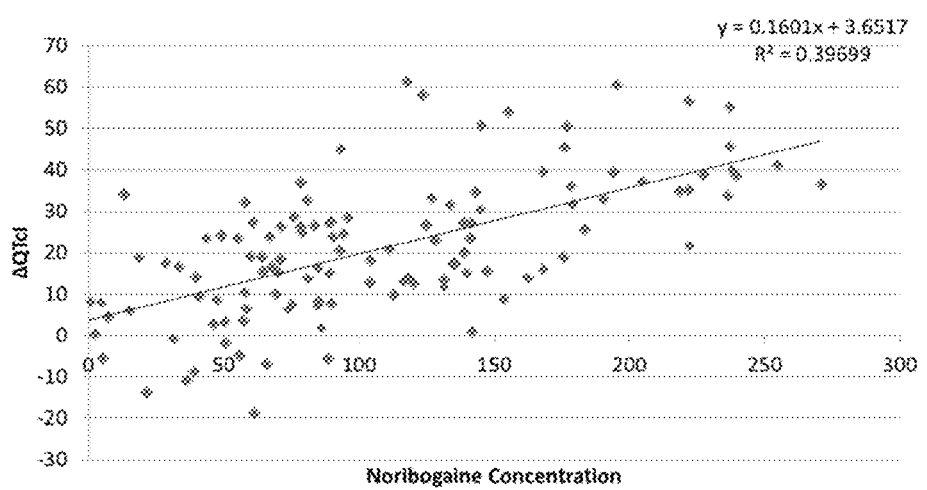
FIG. 9B illustrates the correlation between serum noribogaine concentration and $\Delta$QTcl for each patient over time. The equation of the line is given.

Patients' QT intervals were evaluated at regular time points throughout the study. FIG. 9A shows the average change in QT interval ($\Delta$QTcI, i.e., QT interval prolongation) over the first 24 hours post noribogaine (or placebo) administration. FIG. 9B shows the estimated correlation between noribogaine concentration and change in QT interval. There is a dose-dependent increase in QT interval prolongation that is correlated with the serum concentration of noribogaine.

Based on above data, it is believed that the therapeutic window for a single bolus dose of noribogaine is bound at the lower end by 50 mg and at the upper end by less than 180 mg. In particular, the therapeutic serum concentration in vivo appears to be between about 50 ng/mL and about 180 ng/mL.

What is claimed is:

1. A method for screening an opioid-addicted patient to determine the patient's tolerance for a therapeutic dose of noribogaine or pharmaceutically acceptable salt and/or solvate thereof, the method comprising:
    measuring the patient's pre-administration QT interval;
    administering orally or by direct blood stream delivery to the patient a sub-therapeutic dose of 60 mg to 100 mg of noribogaine or pharmaceutically acceptable salt thereof;
    measuring the patient's post-administration QT interval; and
    comparing the difference between the pre-administration QT interval and post-administration QT interval with an expected change in QT interval for the dose administered based on a known average change in QT interval for the sub-therapeutic dose, wherein the patient is tolerant of a therapeutic dose of noribogaine or pharmaceutically acceptable salt and/or solvate thereof if the difference is not more than the expected change.

2. The method of claim 1, further comprising administering to the patient the therapeutic dose of noribogaine or pharmaceutically acceptable salt and/or solvate thereof or discontinuing noribogaine treatment, wherein a therapeutic dose is administered if the difference is not more than the expected change.

3. The method of claim 2, wherein the therapeutic dose provides an average serum concentration of 50 ng/mL to 180 ng/mL, said concentration being sufficient to inhibit or ameliorate opioid addiction while resulting in prolongation of the patient's QT interval of less than about 50 ms.

4. The method of claim 2, further comprising:
    a) administering an initial dose of noribogaine or pharmaceutically acceptable salt or solvate thereof, wherein the initial dose provides an average serum concentration of 50 ng/mL to 180 ng/mL; and
    b) administering at least one additional dose of noribogaine or pharmaceutically acceptable salt or solvate thereof, such that the at least one additional dose maintains the average serum concentration of 50 ng/mL to 180 ng/mL for a period of time.

5. The method of claim 2, wherein the therapeutic dose is administered in one or more dosings.

6. The method of claim 1, wherein the sub-therapeutic dose is administered in one or more dosings.

7. The method of claim 1, wherein the sub-therapeutic dose is 80% or less than the therapeutic dose.

8. The method of claim 1, wherein the sub-therapeutic dose is 70% or less than the therapeutic dose.

9. The method of claim 1, wherein the sub-therapeutic dose is about 90 mg.

10. The method of claim 3, wherein the therapeutic dose is between about 50 mg and about 120 mg per day.

* * * * *